(12) United States Patent
Vale, Jr. et al.

(10) Patent No.: US 6,214,797 B1
(45) Date of Patent: Apr. 10, 2001

(54) UROCORTIN PEPTIDES, NUCLEIC ACID ENCODING SAME METHODS FOR USING SAME

(75) Inventors: Wylie W. Vale, Jr., La Jolla; Joan Vaughan, Oceanside; Cynthia J. Donaldson; Kathy A. Lewis, both of San Diego; Paul Sawchenko, Encinitas; Jean E. F. Rivier; Marilyn H. Perrin, both of La Jolla, all of CA (US)

(73) Assignee: The Salk Institute for Biological Studies, San Diego, CA (US)

( * ) Notice: Subject to any disclaimer, the term of this patent is extended or adjusted under 35 U.S.C. 154(b) by 0 days.

(21) Appl. No.: 08/981,189

(22) PCT Filed: Jun. 12, 1996

(86) PCT No.: PCT/US96/10240

§ 371 Date: Dec. 10, 1997

§ 102(e) Date: Dec. 10, 1997

(87) PCT Pub. No.: WO97/00063

PCT Pub. Date: Jan. 3, 1997

Related U.S. Application Data

(60) Provisional application No. 60/028,144, filed on Jun. 13, 1995, and provisional application No. 60/002,223, filed on Aug. 11, 1995.

(51) Int. Cl.[7] .................. A61K 38/17; C07K 14/47; C07H 21/04; C12N 15/16
(52) U.S. Cl. ................... 514/12; 514/2; 530/300; 530/317; 530/324; 536/23.51; 536/24.3
(58) Field of Search ................ 530/300, 324, 530/345, 317; 435/69.1, 69.4; 514/2, 12; 536/23.51, 24.3

(56) References Cited

U.S. PATENT DOCUMENTS 4,908,352 3/1990 Lederis et al. .

FOREIGN PATENT DOCUMENTS

| | | |
|---|---|---|
| WO 89/12646 | 12/1989 | (WO) . |
| WO 90/03392 | 4/1990 | (WO) . |
| WO 92/22576 | 12/1992 | (WO) . |
| WO 95/34651 | 12/1995 | (WO) . |

OTHER PUBLICATIONS

Vaughan, et al., *Nature*, vol. 378, pp. 287–292, Nov. 16, 1995, "Urocortin, a mammalian neuropeptide related to fish urotensin I and to corticotropin–releasing factor".

Lovenberg, et al., (Neurobiology), *PNAS*, vol. 92, pp, 836–840, Jan. 1995, "Cloning and characterization of a functionally distinct corticotropin–releasing factor receptor subtype from rat brain".

Masiakowski et al. J. Biol. Chem 267(36): 26181–26190, 1992.*

Stoltzfus et al. J. Biol. Chem 267(10): 6570–6575, 1992.*

* cited by examiner

*Primary Examiner*—Christine J. Saoud
(74) *Attorney, Agent, or Firm*—Fitch, Even, Tabin & Flannery

(57) ABSTRACT

Urocortin (Ucn) is a native mammalian peptide generally related to Urotensin I and Corticotropin Releasing Factor (CRF). Human Ucn has the formula: Asp-Asn-Pro-Ser-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-$NH_2$ (SEQ ID NO:15). Rat-derived Ucn is identical but for 2 substitutions, $Asp^2$ for $Asn^2$ and $Pro^4$ for $Ser^4$. Ucn or analogs thereof or pharmaceutically acceptable salts can be administered to humans and other mammals to achieve substantial elevation of ACTH, β-endorphin, β-lipotropin, other products of the pro-opiomelanocortin gene and corticosterone. They can also be used to lower blood pressure over an extended period of time, as stimulants to elevate mood and to improve memory and learning performance, as well as diagnostically. Shortened fragments may be administered to release endogenous CRF and/or Ucn in the brain and peripherally. Ucn antagonists can be used to block the action of Ucn and/or CRF, as can antibodies to Ucn. Labelled Ucn agonists and antagonists can be used in drug screening assays along with CRF receptors; they may also be used diagnostically along with Ucn antibodies.

22 Claims, No Drawings

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:1:

```
Ser Gln Glu Pro Pro Ile Ser Leu Asp Leu Thr Phe His Leu Leu Arg
 1               5                  10                  15

Glu Val Leu Glu Met Thr Lys Ala Asp Gln Leu Ala Gln Gln Ala His
            20                  25                  30

Ser Asn Arg Lys Leu Leu Asp Ile Ala
            35                  40
```

(2) INFORMATION FOR SEQ ID NO:2:

(i) SEQUENCE CHARACTERISTICS:
      (A) LENGTH: 40 amino acids
      (B) TYPE: amino acid
      (D) TOPOLOGY: linear (ii) MOLECULE TYPE: peptide (xi) SEQUENCE DESCRIPTION: SEQ ID NO:2:

```
Glu Gly Pro Pro Ile Ser Ile Asp Leu Ser Leu Glu Leu Leu Arg Lys
 1               5                  10                  15

Met Ile Glu Ile Glu Lys Gln Glu Lys Glu Lys Gln Gln Ala Ala Asn
            20                  25                  30

Asn Arg Leu Leu Leu Asp Thr Ile
            35                  40
```

(2) INFORMATION FOR SEQ ID NO:3:

(i) SEQUENCE CHARACTERISTICS:
      (A) LENGTH: 41 amino acids
      (B) TYPE: amino acid
      (D) TOPOLOGY: linear (ii) MOLECULE TYPE: peptide (xi) SEQUENCE DESCRIPTION: SEQ ID NO:3:

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

(2) INFORMATION FOR SEQ ID NO:4:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:4:

Asn Asp Asp Pro Pro Ile Ser Ile Asp Leu Thr Phe His Leu Leu Arg
1               5                   10                  15

Asn Met Ile Glu Met Ala Arg Ile Glu Asn Glu Arg Glu Gln Ala Gly
            20                  25                  30

Leu Asn Arg Lys Tyr Leu Asp Glu Val
        35                  40

(2) INFORMATION FOR SEQ ID NO:5:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:5:

Asn Asp Asp Pro Pro Ile Ser Ile Asp Leu Thr Phe His Leu Leu Arg
1               5                   10                  15

Asn Met Ile Glu Met Ala Arg Asn Glu Asn Gln Arg Glu Gln Ala Gly
            20                  25                  30

Leu Asn Arg Lys Tyr Leu Asp Glu Val
        35                  40

(2) INFORMATION FOR SEQ ID NO:6:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:6:

Ser Glu Glu Pro Pro Met Ser Ile Asp Leu Thr Phe His Met Leu Arg
1               5                   10                  15

Asn Met Ile His Arg Ala Lys Met Glu Gly Glu Arg Glu Gln Ala Leu
            20                  25                  30

Ile Asn Arg Asn Leu Leu Asp Glu Val
        35                  40

(2) INFORMATION FOR SEQ ID NO:7:

(i) SEQUENCE CHARACTERISTICS:
        (A) LENGTH: 41 amino acids (B) TYPE: amino acid
          (D) TOPOLOGY: linear (ii) MOLECULE TYPE: peptide (xi) SEQUENCE DESCRIPTION: SEQ ID NO:7:

Ser Glu Glu Pro Pro Ile Ser Leu Asp Leu Thr Phe His Leu Leu Arg
 1               5                  10                  15

Glu Val Leu Glu Met Ala Arg Ala Glu Gln Leu Ala Gln Gln Ala His
                20                  25                  30

Ser Asn Arg Lys Met Met Glu Ile Phe
            35                  40

(2) INFORMATION FOR SEQ ID NO:8:

(i) SEQUENCE CHARACTERISTICS:
        (A) LENGTH: 40 amino acids
        (B) TYPE: amino acid
        (D) TOPOLOGY: linear (ii) MOLECULE TYPE: peptide (xi) SEQUENCE DESCRIPTION: SEQ ID NO:8:

Asp Asp Pro Pro Leu Ser Ile Asp Leu Thr Phe His Leu Leu Arg Thr
 1               5                  10                  15

Leu Leu Glu Leu Ala Arg Thr Gln Ser Gln Arg Glu Arg Ala Glu Gln
                20                  25                  30

Asn Arg Ile Ile Phe Asp Ser Val
            35                  40

(2) INFORMATION FOR SEQ ID NO:9:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (A) ORGANISM: Rat Brain (vii) IMMEDIATE SOURCE:
          (B) CLONE: CK21

(ix) FEATURE:
         (A) NAME/KEY: CDS
         (B) LOCATION: 1..120

(xi) SEQUENCE DESCRIPTION: SEQ ID NO:9:

GAC GAC CCG CCG TTG TCC ATC GAC CTC ACC TTC CAC CTG CTG CGG ACC      48
Asp Asp Pro Pro Leu Ser Ile Asp Leu Thr Phe His Leu Leu Arg Thr
 1               5                  10                  15

CTG CTA GAG CTA GCT CGG ACA CAG AGC CAG CGC GAG CGC GCA GAG CAG      96
Leu Leu Glu Leu Ala Arg Thr Gln Ser Gln Arg Glu Arg Ala Glu Gln
                20                  25                  30

AAC CGC ATC ATA TTC GAT TCG GTG GGCAAGTGA                            129
Asn Arg Ile Ile Phe Asp Ser Val
            35                  40

(2) INFORMATION FOR SEQ ID NO:10:

(i) SEQUENCE CHARISTICS:
    (A) LENGTH: 415 amino acids
    (B) TYPE: amino acid
    (D) TOPOLOGY: linear (ii) MOLECULE TYPE: protein (ix) FEATURE:
    (A) NAME/KEY: Protein
    (B) LOCATION: 1..415
    (D) OTHER INFORMATION: /note= "Human Pituitary
        CRF-Receptor-R1"

(x) PUBLICATION INFORMATION:
    (A) AUTHORS: Perrin, Marilyn H
             Donaldson, Cynthia J
             Chen, Ruoping
             Lewis, Kathy A
             Vale, Wylie W
    (B) TITLE: Cloning and Functional Expression of a Rat
        Brain Corticotropin Releasing Factor (CRF)
        Receptor
    (C) JOURNAL: Endocrinology
    (D) VOLUME: 133
    (E) ISSUE: 6
    (F) PAGES: 3058-3061
    (G) DATE: 1993

(xi) SEQUENCE DESCRIPTION: SEQ ID NO:10:

```
Met Gly Arg Arg Pro Gln Leu Arg Leu Val Lys Ala Leu Leu Leu Leu
 1               5                  10                  15

Gly Leu Asn Pro Val Ser Thr Ser Leu Gln Asp Gln Arg Cys Glu Asn
                20                  25                  30

Leu Ser Leu Thr Ser Asn Val Ser Gly Leu Gln Cys Asn Ala Ser Val
            35                  40                  45

Asp Leu Ile Gly Thr Cys Trp Pro Arg Ser Pro Ala Gly Gln Leu Val
 50                  55                  60

Val Arg Pro Cys Pro Ala Phe Phe Tyr Gly Val Arg Tyr Asn Thr Thr
 65                  70                  75                  80

Asn Asn Gly Tyr Arg Glu Cys Leu Ala Asn Gly Ser Trp Ala Ala Arg
                85                  90                  95

Val Asn Tyr Ser Glu Cys Gln Glu Ile Leu Asn Glu Glu Lys Lys Ser
            100                 105                 110

Lys Val His Tyr His Val Ala Val Ile Ile Asn Tyr Leu Gly His Cys
        115                 120                 125

Ile Ser Leu Val Ala Leu Leu Val Ala Phe Val Leu Phe Leu Arg Leu
130                 135                 140

Arg Ser Ile Arg Cys Leu Arg Asn Ile Ile His Trp Asn Leu Ile Ser
145                 150                 155                 160

Ala Phe Ile Leu Arg Asn Ala Thr Trp Phe Val Val Gln Leu Thr Val
                165                 170                 175

Ser Pro Glu Val His Gln Ser Asn Val Ala Trp Cys Arg Leu Val Thr
            180                 185                 190

Ala Ala Tyr Asn Tyr Phe His Val Thr Asn Phe Phe Trp Met Phe Gly
        195                 200                 205

Glu Gly Cys Tyr Leu His Thr Ala Ile Val Leu Thr Tyr Ser Thr Asp
210                 215                 220

Arg Leu Arg Lys Trp Met Phe Val Cys Ile Gly Trp Gly Val Pro Phe
225                 230                 235                 240

Pro Ile Ile Val Ala Trp Ala Ile Gly Lys Leu His Tyr Asp Asn Glu
                245                 250                 255

Lys Cys Trp Phe Gly Lys Arg Pro Gly Val Tyr Thr Asp Tyr Ile Tyr
```

```
                        260                 265                 270
Gln Gly Pro Met Ile Leu Val Leu Leu Ile Asn Phe Ile Phe Leu Phe
                275                 280                 285

Asn Ile Val Arg Ile Leu Met Thr Lys Leu Arg Ala Ser Thr Thr Ser
        290                 295                 300

Glu Thr Ile Gln Tyr Arg Lys Ala Val Lys Ala Thr Leu Val Leu Leu
305                 310                 315                 320

Pro Leu Leu Gly Ile Thr Tyr Met Leu Phe Phe Val Asn Pro Gly Glu
                325                 330                 335

Asp Glu Val Ser Arg Val Val Phe Ile Tyr Phe Asn Ser Phe Leu Glu
                340                 345                 350

Ser Phe Gln Gly Phe Phe Val Ser Val Phe Tyr Cys Phe Leu Asn Ser
                355                 360                 365

Glu Val Arg Ser Ala Ile Arg Lys Arg Trp Arg Arg Trp Gln Asp Lys
        370                 375                 380

His Ser Ile Arg Ala Arg Val Ala Arg Ala Met Ser Ile Pro Thr Ser
385                 390                 395                 400

Pro Thr Arg Val Ser Phe His Ser Ile Lys Gln Ser Thr Ala Val
                405                 410                 415
```

(2) INFORMATION FOR SEQ ID NO:11:

(i) SEQUENCE CHARACTERISTICS:
        (A) LENGTH: 431 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..431
        (D) OTHER INFORMATION: /note= "Product-mouse heart derived
            CRF-R2 Long Form"

(x) PUBLICATION INFORMATION:
        (A) AUTHORS: Perrin, Marilyn
            Donaldson, Cynthia
            Chen, Ruoping
            Blount, Amy
            Berggren, Travis
            Bilezikjian, Louise
            Sawchenko, Paul
            Vale, Wylie
        (B) TITLE: Identification of a second
            corticotropin-releasing factor receptor gene and
            characterization of a cDNA expressed in heart
        (C) JOURNAL: Proc. Natl. Acad. Sci. U.S.A.
        (D) VOLUME: 92
        (F) PAGES: 2969-2973
        (G) DATE: March-1995

(xi) SEQUENCE DESCRIPTION: SEQ ID NO:11:

```
Met Gly Thr Pro Gly Ser Leu Pro Ser Ala Gln Leu Leu Leu Cys Leu
1               5                   10                  15

Phe Ser Leu Leu Pro Val Leu Gln Val Ala Gln Pro Gln Ala Pro
                20                  25                  30

Gln Asp Gln Pro Leu Trp Thr Leu Leu Glu Gln Tyr Cys His Arg Thr
            35                  40                  45

Thr Ile Gly Asn Phe Ser Gly Pro Tyr Thr Tyr Cys Asn Thr Thr Leu
        50                  55                  60

Asp Gln Ile Gly Thr Cys Trp Pro Gln Ser Ala Pro Gly Ala Leu Val
65                  70                  75                  80
```

```
Glu Arg Pro Cys Pro Glu Tyr Phe Asn Gly Ile Lys Tyr Asn Thr Thr
                    85                  90                  95

Arg Asn Ala Tyr Arg Glu Cys Leu Glu Asn Gly Thr Trp Ala Ser Arg
            100                 105                 110

Val Asn Tyr Ser His Cys Glu Pro Ile Leu Asp Asp Lys Gln Arg Lys
        115                 120                 125

Tyr Asp Leu His Tyr Arg Ile Ala Leu Ile Val Asn Tyr Leu Gly His
    130                 135                 140

Cys Val Ser Val Val Ala Leu Val Ala Ala Phe Leu Leu Phe Leu Val
145                 150                 155                 160

Leu Arg Ser Ile Arg Cys Leu Arg Asn Val Ile His Trp Asn Leu Ile
                165                 170                 175

Thr Thr Phe Ile Leu Arg Asn Ile Ala Trp Phe Leu Leu Gln Leu Ile
                180                 185                 190

Asp His Glu Val His Glu Gly Asn Glu Val Trp Cys Arg Cys Ile Thr
            195                 200                 205

Thr Ile Phe Asn Tyr Phe Val Val Thr Asn Phe Phe Trp Met Phe Val
        210                 215                 220

Glu Gly Cys Tyr Leu His Thr Ala Ile Val Met Thr Tyr Ser Thr Glu
225                 230                 235                 240

His Leu Arg Lys Trp Leu Phe Leu Phe Ile Gly Trp Cys Ile Pro Cys
                245                 250                 255

Pro Ile Ile Ile Ala Trp Ala Val Gly Lys Leu Tyr Tyr Glu Asn Glu
                260                 265                 270

Gln Cys Trp Phe Gly Lys Glu Ala Gly Asp Leu Val Asp Tyr Ile Tyr
            275                 280                 285

Gln Gly Pro Val Met Leu Val Leu Leu Ile Asn Phe Val Phe Leu Phe
    290                 295                 300

Asn Ile Val Arg Ile Leu Met Thr Lys Leu Arg Ala Ser Thr Thr Ser
305                 310                 315                 320

Glu Thr Ile Gln Tyr Arg Lys Ala Val Lys Ala Thr Leu Val Leu Leu
                325                 330                 335

Pro Leu Leu Gly Ile Thr Tyr Met Leu Phe Phe Val Asn Pro Gly Glu
                340                 345                 350

Asp Asp Leu Ser Gln Ile Val Phe Ile Tyr Phe Asn Ser Phe Leu Gln
            355                 360                 365

Ser Phe Gln Gly Phe Phe Val Ser Val Phe Tyr Cys Phe Phe Asn Gly
    370                 375                 380

Glu Val Arg Ala Ala Leu Arg Lys Arg Trp His Arg Trp Gln Asp His
385                 390                 395                 400

His Ala Leu Arg Val Pro Val Ala Arg Ala Met Ser Ile Pro Thr Ser
                405                 410                 415

Pro Thr Arg Ile Ser Phe His Ser Ile Lys Gln Thr Ala Ala Val
                420                 425                 430

(2) INFORMATION FOR SEQ ID NO:12:

(i) SEQUENCE CHARACTERISTICS:
        (A) LENGTH: 411 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..411
```

(D) OTHER INFORMATION: /note= "Rat CRF-R2 Short Form"

(x) PUBLICATION INFORMATION:
    (A) AUTHORS: Lovenberg, Timothy W
        Liaw, Chen W
        Grigoriadis, Dimitri E
        Clevenger, William
        Chalmers, Derek T
        DeSouza, Errol B
        Oltersdorf, Tilman
    (B) TITLE: Cloning and characterization of a
        functionally distinct corticotropin-releasing
        factor receptor subtype from rat brain
    (C) JOURNAL: Proc. Natl. Acad. Sci. U.S.A.
    (D) VOLUME: 92
    (F) PAGES: 836-840
    (G) DATE: January-1995

(xi) SEQUENCE DESCRIPTION: SEQ ID NO:12:

```
Met Asp Ala Ala Leu Leu Leu Ser Leu Leu Glu Ala Asn Cys Ser Leu
 1               5                  10                  15

Ala Leu Ala Glu Glu Leu Leu Leu Asp Gly Trp Gly Glu Pro Pro Asp
            20                  25                  30

Pro Glu Gly Pro Tyr Ser Tyr Cys Asn Thr Thr Leu Asp Gln Ile Gly
                35                  40                  45

Thr Cys Trp Pro Gln Ser Ala Pro Gly Ala Leu Val Glu Arg Pro Cys
 50                  55                  60

Pro Glu Tyr Phe Asn Gly Ile Lys Tyr Asn Thr Thr Arg Asn Ala Tyr
 65                  70                  75                  80

Arg Glu Cys Leu Glu Asn Gly Thr Trp Ala Ser Arg Ile Asn Tyr Ser
                85                  90                  95

His Cys Glu Pro Ile Leu Asp Asp Lys Gln Arg Lys Tyr Asp Leu His
                100                 105                 110

Tyr Arg Ile Ala Leu Ile Ile Asn Tyr Leu Gly His Cys Val Ser Val
            115                 120                 125

Val Ala Leu Val Ala Ala Phe Leu Leu Phe Leu Val Leu Arg Ser Ile
130                 135                 140

Arg Cys Leu Arg Asn Val Ile His Trp Asn Leu Ile Thr Thr Phe Ile
145                 150                 155                 160

Leu Arg Asn Ile Thr Trp Phe Leu Leu Gln Leu Ile Asp His Glu Val
                165                 170                 175

His Glu Gly Asn Glu Val Trp Cys Arg Cys Val Thr Thr Ile Phe Asn
            180                 185                 190

Tyr Phe Val Val Thr Asn Phe Phe Trp Met Phe Val Glu Gly Cys Tyr
        195                 200                 205

Leu His Thr Ala Ile Val Met Thr Tyr Ser Thr Glu His Leu Arg Lys
    210                 215                 220

Trp Leu Phe Leu Phe Ile Gly Trp Cys Ile Pro Cys Pro Ile Ile Val
225                 230                 235                 240

Ala Trp Ala Val Gly Lys Leu Tyr Tyr Glu Asn Glu Gln Cys Trp Phe
                245                 250                 255

Gly Lys Glu Pro Gly Asp Leu Val Asp Tyr Ile Tyr Gln Gly Pro Ile
            260                 265                 270

Ile Leu Val Leu Leu Ile Asn Phe Val Phe Leu Phe Asn Ile Val Arg
        275                 280                 285

Ile Leu Met Thr Lys Leu Arg Ala Ser Thr Thr Ser Glu Thr Ile Gln
    290                 295                 300

Tyr Arg Lys Ala Val Lys Ala Thr Leu Val Leu Leu Pro Leu Leu Gly
305                 310                 315                 320
```

```
Ile Thr Tyr Met Leu Phe Phe Val Asn Pro Gly Glu Asp Asp Leu Ser
                325                 330                 335

Gln Ile Val Phe Ile Tyr Phe Asn Ser Phe Leu Gln Ser Phe Gln Gly
            340                 345                 350

Phe Phe Val Ser Val Phe Tyr Cys Phe Phe Asn Gly Glu Val Arg Ser
            355                 360                 365

Ala Leu Arg Lys Arg Trp His Arg Trp Gln Asp His His Ala Leu Arg
    370                 375                 380

Val Pro Val Ala Arg Ala Met Ser Ile Pro Thr Ser Pro Thr Arg Ile
385                 390                 395                 400

Ser Phe His Ser Ile Lys Gln Thr Ala Ala Val
                405                 410
```

(2) INFORMATION FOR SEQ ID NO:13:

(i) SEQUENCE CHARACTERISTICS:
        (A) LENGTH: 431 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..431
        (D) OTHER INFORMATION: /note= "Rat CRF-R2 Long Form"

(x) PUBLICATION INFORMATION:
        (A) AUTHORS: Lovenberg, Timothy W
            Liaw, Chen W
            Grigoriadis, Dimitri E
            Clevenger, William
            Chalmers, Derek T
            DeSouza, Errol B
            Oltersdorf, Tilman
        (B) TITLE: Cloning and characterization of a
            functionally distinct corticotropin-releasing
            factor receptor subtype from rat brain
        (C) JOURNAL: Proc. Natl. Acad. Sci. U.S.A.
        (D) VOLUME: 92
        (F) PAGES: 836-840
        (G) DATE: January-1995

(xi) SEQUENCE DESCRIPTION: SEQ ID NO:13:

```
Met Gly His Pro Gly Ser Leu Pro Ser Ala Gln Leu Leu Leu Cys Leu
1               5                   10                  15

Tyr Ser Leu Leu Pro Leu Leu Gln Val Ala Gln Pro Gly Arg Pro Leu
                20                  25                  30

Gln Asp Gln Pro Leu Trp Thr Leu Leu Glu Gln Tyr Cys His Arg Thr
            35                  40                  45

Thr Thr Arg Asn Phe Ser Gly Pro Tyr Ser Tyr Cys Asn Thr Thr Leu
    50                  55                  60

Asp Gln Ile Gly Thr Cys Trp Pro Gln Ser Ala Pro Gly Ala Leu Val
65                  70                  75                  80

Glu Arg Pro Cys Pro Glu Tyr Phe Asn Gly Ile Lys Tyr Asn Thr Thr
                85                  90                  95

Arg Asn Ala Tyr Arg Glu Cys Leu Glu Asn Gly Thr Trp Ala Ser Arg
                100                 105                 110

Ile Asn Tyr Ser His Cys Glu Pro Ile Leu Asp Asp Lys Gln Arg Lys
            115                 120                 125

Tyr Asp Leu His Tyr Arg Ile Ala Leu Ile Ile Asn Tyr Leu Gly His
            130                 135                 140
```

-continued

```
Cys Val Ser Val Val Ala Leu Val Ala Ala Phe Leu Leu Phe Leu Val
145                 150                 155                 160

Leu Arg Ser Ile Arg Cys Leu Arg Asn Val Ile His Trp Asn Leu Ile
            165                 170                 175

Thr Thr Phe Ile Leu Arg Asn Ile Thr Trp Phe Leu Leu Gln Leu Ile
            180                 185                 190

Asp His Glu Val His Glu Gly Asn Glu Val Trp Cys Arg Cys Val Thr
            195                 200                 205

Thr Ile Phe Asn Tyr Phe Val Val Thr Asn Phe Phe Trp Met Phe Val
210                 215                 220

Glu Gly Cys Tyr Leu His Thr Ala Ile Val Met Thr Tyr Ser Thr Glu
225                 230                 235                 240

His Leu Arg Lys Trp Leu Phe Leu Phe Ile Gly Trp Cys Ile Pro Cys
            245                 250                 255

Pro Ile Ile Val Ala Trp Ala Val Gly Lys Leu Tyr Tyr Glu Asn Glu
            260                 265                 270

Gln Cys Trp Phe Gly Lys Glu Pro Gly Asp Leu Val Asp Tyr Ile Tyr
            275                 280                 285

Gln Gly Pro Ile Ile Leu Val Leu Leu Ile Asn Phe Val Phe Leu Phe
290                 295                 300

Asn Ile Val Arg Ile Leu Met Thr Lys Leu Arg Ala Ser Thr Thr Ser
305                 310                 315                 320

Glu Thr Ile Gln Tyr Arg Lys Ala Val Lys Ala Thr Leu Val Leu Leu
            325                 330                 335

Pro Leu Leu Gly Ile Thr Tyr Met Leu Phe Phe Val Asn Pro Gly Glu
            340                 345                 350

Asp Asp Leu Ser Gln Ile Val Phe Ile Tyr Phe Asn Ser Phe Leu Gln
            355                 360                 365

Ser Phe Gln Gly Phe Phe Val Ser Val Phe Tyr Cys Phe Phe Asn Gly
            370                 375                 380

Glu Val Arg Ser Ala Leu Arg Lys Arg Trp His Arg Trp Gln Asp His
385                 390                 395                 400

His Ala Leu Arg Val Pro Val Ala Arg Ala Met Ser Ile Pro Thr Ser
            405                 410                 415

Pro Thr Arg Ile Ser Phe His Ser Ile Lys Gln Thr Ala Ala Val
            420                 425                 430
```

(2) INFORMATION FOR SEQ ID NO:14:

(i) SEQUENCE CHARACTERISTICS:
        (A) LENGTH: 40 amino acids
        (B) TYPE: amino acid
        (D) TOPOLOGY: linear (ii) MOLECULE TYPE: peptide (xi) SEQUENCE DESCRIPTION: SEQ ID NO:14:

```
Xaa Xaa Pro Xaa Xaa Ser Xaa Asp Leu Xaa Xaa Xaa Xaa Leu Arg Xaa
1               5                   10                  15

Xaa Xaa Xaa Xaa Xaa Xaa Xaa Xaa Xaa Xaa Xaa Xaa Xaa Ala Xaa Xaa
            20                  25                  30

Asn Arg Xaa Xaa Xaa Xaa Xaa Xaa
            35                  40
```

(2) INFORMATION FOR SEQ ID NO: 15:

(i) SEQUENCE CHARACTERISTICS:

(A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO: 15:

Met Arg Gln Ala Gly Arg Ala Ala Leu Leu Ala Ala Leu Leu Leu Leu
1               5                   10                  15

Val Gln Leu Cys Pro Gly Ser Ser Gln Arg Ser Pro Glu Ala Ala Gly
            20                  25                  30

Val Gln Asp Pro Ser Leu Arg Trp Ser Pro Gly Ala Arg Asn Gln Gly
        35                  40                  45

Gly Gly Ala Arg Ala Leu Leu Leu Leu Ala Glu Arg Phe Pro Arg
    50                  55                  60

Arg Ala Gly Pro Gly Arg Leu Gly Leu Gly Thr Ala Gly Glu Arg Pro
65                  70                  75                  80

Arg Arg Asp Asn Pro Ser Leu Ser Ile Asp Leu Thr Phe His Leu Leu
                85                  90                  95

Arg Thr Leu Leu Glu Leu Ala Arg Thr Gln Ser Gln Arg Glu Arg Ala
            100                 105                 110

Glu Gln Asn Arg Ile Ile Phe Asp Ser Val Gly Lys
        115                 120

(2) INFORMATION FOR SEQ ID NO: 16:

(i) SEQUENCE CHARACTERISTICS:
        (A) LENGTH: 375 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Human Genomic Placental Library (ix) FEATURE:
        (A) NAME/KEY: CDS
        (B) LOCATION:1..375

(xi) SEQUENCE DESCRIPTION: SEQ ID NO: 16:

ATG AGG CAG GCG GGA CGC GCA GCG CTG CTG GCC GCG CTG CTG CTC CTG        48
Met Arg Gln Ala Gly Arg Ala Ala Leu Leu Ala Ala Leu Leu Leu Leu
1               5                   10                  15

GTA CAG CTG TGC CCT GGG AGC AGC CAG AGG AGC CCC GAG GCG GCC GGG        96
Val Gln Leu Cys Pro Gly Ser Ser Gln Arg Ser Pro Glu Ala Ala Gly
            20                  25                  30

GTC CAG GAC CCG AGT CTG CGC TGG AGC CCC GGG GCA CGG AAC CAG GGT       144
Val Gln Asp Pro Ser Leu Arg Trp Ser Pro Gly Ala Arg Asn Gln Gly
        35                  40                  45

GGC GGG GCC CGC GCG CTC CTC TTG CTG CTG GCG GAG CGC TTC CCG CGC       192
Gly Gly Ala Arg Ala Leu Leu Leu Leu Ala Glu Arg Phe Pro Arg
    50                  55                  60

CGC GCG GGG CCC GGC CGA TTG GGA CTC GGG ACG GCA GGC GAG CGG CCG       240
Arg Ala Gly Pro Gly Arg Leu Gly Leu Gly Thr Ala Gly Glu Arg Pro
65                  70                  75                  80

CGG CGG GAC AAC CCT TCT CTG TCC ATT GAC CTC ACC TTT CAC CTG CTG       288
Arg Arg Asp Asn Pro Ser Leu Ser Ile Asp Leu Thr Phe His Leu Leu
                85                  90                  95

```
CGG ACC CTG CTG GAG CTG GCG CGG ACG CAG AGC CAG CGG GAG CGC GCC      336
Arg Thr Leu Leu Glu Leu Ala Arg Thr Gln Ser Gln Arg Glu Arg Ala
            100                 105                 110

GAG CAG AAC CGC ATC ATA TTC GAC TCG GTG GGC AAG TGA                  375
Glu Gln Asn Arg Ile Ile Phe Asp Ser Val Gly Lys  *
            115                 120                 125
```

(2) INFORMATION FOR SEQ ID NO:17:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (xi) SEQUENCE DESCRIPTION: SEQ ID NO:17:

```
Tyr Asp Asp Pro Pro Leu Ser Ile Asp Leu Thr Phe His Leu Leu Arg Thr
 1               5                  10                  15

Leu Leu Glu Leu Ala Arg Thr Gln Ser Gln Arg Glu Arg Ala Glu Gln
            20                  25                  30

Asn Arg Ile Ile Phe Asp Ser Val
            35                  40
```

(2) INFORMATION FOR SEQ ID NO: 18:

(i) SEQUENCE CHARACTERISTICS:
        (A) LENGTH: 27 bases
        (B) TYPE: nucleic acid
        (C) STRANDEDNESS: single
        (D) TOPOLOGY: linear (xi) SEQUENCE DESCRIPTION: SEQ ID NO: 18:

```
TGCAGGCGAG CGGCAACGAC GAGACGA                                         27
```

(2) INFORMATION FOR SEQ ID NO: 19:

(i) SEQUENCE CHARACTERISTICS:
        (A) LENGTH: 28 bases
        (B) TYPE: nucleic acid
        (C) STRANDEDNESS: single
        (D) TOPOLOGY: linear (xi) SEQUENCE DESCRIPTION: SEQ ID NO: 19:

```
ATACGGGGCC GATCACTTGC CCACCGAG                                        28
```

UROCORTIN PEPTIDES, NUCLEIC ACID ENCODING SAME METHODS FOR USING SAME

This application is a national stage entry of PCT/US96/10240 which claims priority from Provisional Applications Ser. Nos. 60/028,144, filed Jun. 13, 1995 and 60/002,223, filed Aug. 11, 1995.

This invention was made with Government support under Grant Number DK-26741 awarded by the National Institutes of Health. The Government has certain rights in this invention.

This application claims priority from Provisional Application Ser. No. 60/002,223, filed Aug. 11, 1995 and from Ser. No. 08/490,314, filed Jun. 13, 1995, which is being converted to a provisional application.

This invention is directed to peptide hormones, to methods for treatment of mammals, including humans, using such peptides, to antibodies which bind such peptides, to methods for diagnosis and drug screening using such peptides and/or antibodies, and to nucleic acid encoding such peptides. More specifically, the invention relates to a native peptide having certain pharmacological properties in common with urotensin and with CRF, which is termed urocortin (Ucn), to analogs and fragments thereof (broadly termed Ucn-like peptides), to pharmaceutical compositions containing such Ucn peptides and to methods of treatment of mammals, method of diagnosis and methods of screening using such Ucn peptides and antibodies thereto.

BACKGROUND OF THE INVENTION

Experimental and clinical observations have supported the concept that the hypothalamus plays a key role in the regulation of adenohypophysial corticotropic cells secretory functions. Although over 40 years ago, Guillemin, Rosenberg and Saffran and Schally independently demonstrated the presence of factors in hypothalamus which would increase the rate of ACTH secretion by the pituitary gland incubated in vitro or maintained in an organ culture, a physiologic corticotropin releasing factor (CRF) was not characterized until ovine CRF (oCRF) was characterized in 1981. It was disclosed in U.S. Pat. No. 4,415,558, as having the amino acid sequence (SEQ ID NO:1):
H-Ser-Gln-Glu-Pro-Pro-Ile-Ser-Leu-Asp-Leu-Thr-Phe-His-Leu-Leu-Arg-Glu-Val-Leu-Glu-Met-Thr-Lys-Ala-Asp-Gln-Leu-Ala-Gln-Gln-Ala-His-Ser-Asn-Arg-Lys-Leu-Leu-Asp-Ile-Ala-$NH_2$.

Although originally isolated and characterized on the basis of its role in this hypothalamopituitary-adrenal (HPA) axis, CRF has been found to be distributed broadly throughout the central nervous system as well as in extraneural tissues, such as the adrenal glands, placenta and testes, where it may also act as a paracrine regulator or a neurotransmitter. Moreover, the likely involvement of CRF in affective disorders, such as anxiety, depression, alcoholism and anorexia nervosa, and in modulating reproduction and immune responses suggests that changes in CRF expression may have important physiological and pathophysiological consequences. For example, perturbations in the regulatory loops comprising the HPA axis often produce chronically elevated levels of circulating glucocorticoids; such patients display the physical hallmarks of Cushing's syndrome, including truncal obesity, muscle-wasting, and reduced fertility.

In addition to its role in mediating activation of the hypothalamic-pituitary-adrenal, CRF has also been shown to modulate autonomic and behavioral changes, some of which occur during the stress response. Many of these behavioral changes have been shown to occur independently of HPA activation in that they are not duplicated by dexamethasone treatment and are insensitive to hypophysectomy. In addition, direct infusion of CRF into the CNS mimics autonomic and behavioral responses to a variety of stressors. Because peripheral administration of CRF or a CRF antagonist fails to affect certain of these changes, it appears that CRF exhibits a direct brain action with respect to such functions, which include appetite suppression, increased arousal and learning ability. However, CRF antagonists given peripherally attenuate stress-mediated increases in ACTH secretion, and when delivered into the cerebral ventricles can mitigate stress-induced changes in autonomic activity and behavior.

As a result of the extensive anatomical distribution and multiple biological actions of CRF, this regulatory peptide is believed to be involved in the regulation of numerous biological processes. CRF has also been implicated in the regulation of inflammatory responses. Although it has been observed that CRF plays a pro-inflammatory role in certain animal models, CRF appears to suppress inflammation in others by reducing injury-induced increases in vascular permeability.

In about 1981, a 40-residue amidated peptide generally similar to CRF was isolated from the skin of the South American frog *Phyllomedusa sauvagei;* it is referred to as sauvagine. It was characterized by Erspamer et al. and was described in *Regulatory Peptides,* Vol. 2 (1981), pp. 1–13. Sauvagine has the amino acid sequence (SEQ ID NO:2): pGlu-Gly-Pro-Pro-Ile-Ser-Ile-Asp-Leu-Ser-Leu-Glu-Leu-Leu-Arg-Lys-Met-Ile-Glu-Ile-Glu-Lys-Gln-Glu-Lys-Glu-Lys-Gln-Gln-Ala-Ala-Asn-Asn-Arg-Leu-Leu-Leu-Asp-Thr-Ile-$NH_2$. When given intravenously (iv), sauvagine and oCRF have been reported to cause vasodilation of the mesenteric arteries so as to lower blood pressure in mammals and also in stimulating the secretion of ACTH and β-endorphin. However, when administered intracerebroventricularly (icv), there is an elevation of heart rate and mean arterial blood pressure, which are secondary to activation of the sympathetic nervous system.

Rat CRF (rCRF) was isolated, purified and characterized in about 1982–1983 as a hentetracontapeptide having the amino acid sequence (SEQ ID NO:3):
H-Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Leu-Met-Glu-Ile-Ile-$NH_2$. The formula of human CRF was subsequently determined to be the same as that of rCRF. The compound is often referred to as r/hCRF and is covered in U.S. Pat. No. 4,489,163.

At about the same time, two homologous polypeptides were isolated from the urophyses of different species of fish. These isolated peptides were generally homologous to CRF, i.e. about 54% homology, and were termed Urotensin I (UI). *Catostomus commersoni* (white sucker or suckerfish) UI is a polypeptide having the amino acid sequence (SEQ ID NO:4):
H-Asn-Asp-Asp-Pro-Pro-Ile-Ser-Ile-Asp-Leu-Thr-Phe-His-Leu-Leu-Arg-Asn-Met-Ile-Glu-Met-Ala-Arg-Ile-Glu-Asn-Glu-Arg-Glu-Gln-Ala-Gly-Leu-Asn-Arg-Lys-Tyr-Leu-Asp-Glu-Val-$NH_2$; it is sometimes referred to as suckerfish (sf) urotensin or sfUI. Its purification and characterization are described in an article by Lederis et al., *Science* Vol. 218, No. 4568, 162–164 (Oct. 8, 1982). The homolog, carp urotensin, was obtained from *Cyprinus carpio* and has the amino acid sequence (SEQ ID NO:5):

H-Asn-Asp-Asp-Pro-Pro-Ile-Ser-Ile-Asp-Leu-Thr-Phe-His-Leu-Leu-Arg-Asn-Met-Ile-Glu-Met-Ala-Arg-Asn-Glu-Asn-Gln-Arg-Glu-Gln-Ala-Gly-Leu-Asn-Arg-Lys-Tyr-Leu-Asp-Glu-Val-NH$_2$. Another urotensin homolog having the following amino acid sequence (SEQ ID NO:6):
H-Ser-Glu-Glu-Pro-Pro-Met-Ser-Ile-Asp-Leu-Thr-Phe-His-Met-Leu-Arg-Asn-Met-Ile-His-Arg-Ala-Lys-Met-Glu-Gly-Glu-Arg-Glu-Gln-Ala-Leu-Ile-Asn-Arg-Asn-Leu-Leu-Asp-Glu-Val-NH$_2$ was later isolated from the urophyses of *Hippoglossoides elassodon* or Flathead (Maggy) Sole; it is sometimes referred to as Maggy urotensin. Synthetic UIs have been found to also stimulate ACTH and β-endorphin activities in vitro and in vivo and to have many of the same general biological activities of CRFs and sauvagine.

Since the discovery of the original discoveries of CRFs in mammals and urotensins in fish, CRFs have now been shown to exist in other animal species. For example, fish CRF was found to be a 41-residue peptide having high homology to r/hCRF; it has the amino acid sequence (SEQ ID NO:7): H-Ser-Glu-Glu-Pro-Pro-Ile-Ser-Leu-Asp-Leu-Thr-Phe-His-Leu-Leu-Arg-Glu-Val-Leu-Glu-Met-Ala-Arg-Ala-Glu-Gln-Leu-Ala-Gln-Gln-Ala-His-Ser-Asn-Arg-Lys-Met-Met-Glu-Ile-Phe-NH$_2$. Synthetic fish CRF (fCRF) stimulates ACTH and β-endorphin activities in vitro and in vivo and has similar biological activities to mammalian CRFs. Because of the high homology between fCRF and r/hCRF, it is thought that other mammalian hormones may exist which would be the counterparts of urotensin and/or sauvagine.

SUMMARY OF THE INVENTION

Another peptide 40 residues in length has now been discovered, which is related to urotensin and CRF; it is arbitrarily referred to as urocortin (Ucn). It has less than 50% homology with rat/human CRF. Although it has the same length as sauvagine, it shares less than 40% homology with sauvagine. It has 62.5% homology with the closest urotensin sequence, i.e. carp urotensin. Thus Ucn has less than about 80% homology with any other previously known native peptide. Rat Ucn has the following amino acid sequence (SEQ ID NO:8): Asp-Asp-Pro-Pro-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$. Human Ucn has the following amino acid sequence (residues 83–122 of SEQ ID NO:15): Asp-Asn-Pro-Ser-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$. Thus, hUcn is the same as rUcn except for Asn$^2$ and Ser$^4$. Ucn has biological properties which are considered to generally resemble those of known CRFs, urotensins and sauvagine but is more biopotent in a number of respects.

The present invention provides Ucn-like peptides, including human and rat Ucn and Analogs thereof, which have substantially all the properties of known CRFs. These Ucn-like peptides not only are potent hypotensive agents, but they have additional pharmacological and physiological properties over and beyond those of heretofore known CRFs. More specifically, agonists are provided for the stimulation of the known CRF receptors (referred to as CRF-Rs), i.e., CRF-R1 and CRF-R2 and their splice varients, as well as the putative novel receptor for Ucn.

Ucn competitive antagonists are also provided which bind the CRF-Rs and the putative Ucn receptor with high affinity but do not significantly stimulate or activate such receptors. Such antagonists are broadly created by deleting a sequence of from 7 to 10 residues beginning at the N-terminus from the amino acid sequence of Ucn or from an analog sequence that is substantially the same. Preferably 9 or 10 residues are deleted, and most preferably 9 are deleted. It may be preferred that the shortened N-terminus be acylated with a group having 7 or less carbon atoms, e.g. [Ac-Thr$^{10}$]-Ucn (10–40), and the inclusion of one, two or three other residues at the N-terminus, e.g., Pro$^{10}$, does not markedly affect biopotency. Other substitutions may be effectively made as described hereinafter. Particularly, D-Phe$^{11}$ or D-Tyr$^{11}$ may be present at the N-terminus and/or a lactam bond created between residues 29 and 32. These antagonists can be administered to achieve at least the same physiological effects as the known CRF antagonists, and such more effective methods of treatment are thus provided.

Fragments of Ucn and Ucn Analogs that are useful to block CRF-binding protein (CRF-BP) are further provided which are effective to elevate levels of endogenous peptides normally cleared by the binding protein. More specifically, these Ucn-like peptides and blocking fragments bind to human CRF-binding protein with high affinity and effectively compete with human CRF and human Ucn (hUcn) in the formation of complexes with hCRF-BP; in this manner, they increase the effective in vivo concentration of endogenous hCRF and/or hUcn, as well as the effective concentration of any CRF agonist or CRF antagonist that may be optionally administered along therewith for the purpose of achieving a particular therapeutic purpose. As a result of blocking the effect of CRF-BP, these fragments effectively increase the concentration of endogenous CRF in those regions of the body where CRF-BP is normally present.

The invention also provides pharmaceutical compositions which include such Ucn-like peptides, or nontoxic salts thereof, dispersed in a pharmaceutically acceptable liquid or solid carrier. The administration of such peptides or pharmaceutically acceptable salts thereof to mammals, particularly humans, in accordance with the invention may be carried out for regulation of the secretion of ACTH, β-endorphin, β-lipotropin, other products of the pro-opiomelanocortin (POMC) gene and corticosterone and/or for lowering blood pressure or increasing coronary flow and/or decreasing swelling and inflammation and/or for affecting learning, mood, behavior, appetite, gastrointestinal and intestinal functions and autonomic nervous system activities.

The invention also provides antibodies which recognize Ucn, and assays for practically employing Ucn and analogs and/or such antibodies for the evaluation of the status of pituitary, cardiovascular, reproductive, hepatic, immune, gastrointestinal or central nervous system functions. For example, such antibodies can be used diagnostically to monitor the level of therapeutically administered Ucn, to facilitate the maintenance of therapeutically effective amounts thereof, as well as for the diagnosis of potential physiological disorders that result from abnormal levels of Ucn. Antibodies of the invention may be therapeutically administered to neutralize endogenous Ucn; alternatively DNA encoding such antibodies might be employed in gene therapy. Anti-Ucn antibodies can also be used to purify CRF-R protein as well as to therapeutically counteract the biological action of Ucn in vivo.

The invention also provides competitive binding assays which are particularly useful for screening candidates for new drugs, e.g. to identify new Ucn-like peptides or other compounds having even greater or more selective binding affinity for CRF receptors and/or for CRF-BP than Ucn, which candidates would therefore be potentially useful as drugs. Such screening assays may be used to screen for potential agonists of Ucn, and other assays employing a labelled Ucn antagonist with high affinity may be used to screen for more potent antagonists of Ucn. In addition, there is provided a method for screening for particularly effective peptides or other compounds which will block the ability of CRF-BP to bind to CRF and Ucn and therefore increase the concentration of CRF and/or Ucn in locations where hCRF-BP is present.

The present invention further provides nucleic acid hybridization probes in the form of isolated nucleic acid encoding native rat Ucn and isolated nucleic acid encoding native human Ucn, which are useful for detecting other Ucn-encoding nucleic acids in biological samples or in libraries of other species in order to identify additional native Ucn or Ucn-like peptides. Such nucleotide sequences also can be used as coding sequences for the recombinant expression of complete Ucn-like peptides or desired biologically active fragments thereof. Fragments of Ucn-encoding nucleic acid can also be employed as primers for PCR amplification of Ucn-encoding DNA. In addition, sequences derived from sequences encoding Ucn or analogs thereof can also be used in gene therapy applications to target the expression of vectors carrying useful genes to specific cell types, and antisense polynucleotides that hybridize with Ucn mRNA may also be used to reduce Ucn levels to counteract certain conditions, e.g. Ucn-secreting tumors. More specifically, the present invention further provides isolated nucleic acids encoding Ucn as well as Ucn analogs containing L-isomers of the 20 natural amino acids. Such nucleic acids comprise:

(a) nucleic acids that encode the amino acid sequence of rat Ucn set forth in SEQ ID NO:8 and that encode the amino acid sequence of human Ucn set forth in SEQ ID NO:15;

(b) nucleic acids which hybridize to the nucleic acids of (a) wherein said hybridizing nucleic acids encode biologically active Ucn-like peptides; or (c) nucleic acids which encode fragments of Ucn or analogs thereof which are CRF-antagonists or CRF-BP blockers.

DETAILED DESCRIPTION OF THE PREFERRED EMBODIMENTS

Unless defined otherwise, all technical and scientific terms used herein have the same meaning as is commonly understood by one of skill in the art to which this invention belongs. The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations to identify the alpha-amino acid residues, and where the amino acid residue has isomeric forms, it is the L-form of the amino acid that is represented unless otherwise expressly indicated, e.g. Ser=L-serine. The nucleotides, which occur in the various nucleic acids, are designated with the standard single-letter designations used routinely in the art.

The term "homology" is used in its usual and well known sense of indicating correspondence between members in a sequence, e.g. either on an amino acid (AA) level or at the nucleotide level. For purposes of this application, the term homologous refers to at least about 70% correspondence, the term substantially homologous refers to a correspondence of at least about 80%, and the term highly homologous refers to a correspondence of at least about 90% or preferably about 95% or higher. The term "homolog" is generally considered to include analogous proteins, peptides and DNA sequences from other mammalian species wherein insignificant changes have evolved but the homolog still performs the same biological function in substantially the same way.

Protein, polypeptide and peptide are used to designate linear sequences of amino acid residues connected one to the other by peptide bonds between the alpha-amino and alpha-carboxy groups of adjacent residues. The term polypeptide may be used interchangeably with peptide and with the term protein; unless otherwise limited, protein is generally used to describe a sequence of about 75 or more residues.

The term "analog" includes any polypeptide having an amino acid residue sequence generally identical to a sequence specifically shown herein, e.g. rUcn or hUcn, wherein one or more residues has been replaced (with at least about 80% and preferably at least about 90% of the residues being the same) and wherein the analog displays the ability to biologically mimic the parent molecule as described herein in some particular function. Preferably, most if not all of such substitutions are replacements of a residue with a functionally similar residue, i.e. conservative substitutions. Examples of such conservative substitutions include: the substitution of one non-polar (hydrophobic) residue, such as isoleucine, valine, alanine, glycine, leucine or methionine for another non-polar residue; the substitution of one polar (hydrophilic) residue for another polar residue, such as arginine for lysine, glutamine for asparagine, threonine for serine; the substitution of one basic residue such as lysine, arginine or histidine for another basic residue; and the substitution of one acidic residue, i.e. aspartic acid or glutamic acid, for the other. The phrase "conservative substitution" is also intended to include the use of a chemically derivatized residue in place of a non-derivatized residue provided that the resultant polypeptide displays the requisite biological activity, e.g. binding activity. For purposes of this application, two peptides are considered to be substantially the same when they only differ from each other by conservative substitutions. Examples of preferred conservative substitutions are set forth in Table 1.

TABLE 1

| Original Residue | Preferred Conservative Substitutions | Most Preferred Substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn; Gln; Lys; Arg | Arg |
| Ile (I) | Leu; Val; Met; Ala; Phe; Nle | Leu |
| Leu (L) | Nle; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala | Leu |
| Pro (P) | Gly | Gly |
| Ser (S) | Thr | Thr |
| Thr (T) | Ser | Ser |
| Trp (W) | Tyr | Tyr |

TABLE 1-continued

| Original Residue | Preferred Conservative Substitutions | Most Preferred Substitution |
|---|---|---|
| Tyr (Y) | Trp; Phe; Thr; Ser | Phe |
| Val (V) | Ile; Leu; Met; Phe Ala; Nle | Leu |

"Chemical derivative" refers to a subject polypeptide having one or more residues chemically derivatized by reaction of a functional side group. Such derivatized polypeptides include, for example, those in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to from O-acyl or O-alkyl derivatives. The imidazole nitrogen of histidine may be derivatized to form N-imbenzylhistidine. Chemical derivatives also include those peptides which contain one or more naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine; and ornithine may be substituted for lysine. Peptides embraced by the present invention also include peptides having one or more residue additions and/or deletions relative to the specific peptide whose sequence is shown herein, so long as the modified peptide maintains the requisite biological activity.

As used herein, the terms "pharmaceutically acceptable", "physiologically tolerable" and grammatical variations thereof, as they refer to compositions, carriers, diluents and reagents, are used interchangeably and represent that the materials are capable of administration to a mammal without the production of undesirable physiological effects such as nausea, dizziness, gastric upset and the like.

The term "biologically active fragment" as used herein refers to (a) a fragment of a peptide of the invention which has been truncated with respect to either the N- or C-termini, or both; or (b) a fragment of nucleic acid corresponding to a coding region for rUcn or a highly homologous native peptide of another mammalian species which has been truncated at the 5' or 3' end, or both, and is useful in antisense applications. The peptide fragment shown performs substantially the same function or a directly related biological function as does the parent.

The phrase "modulating the transactivation of CRF receptors" as used herein refers to administering a therapeutically effective amount of a physiologically tolerable composition containing a Ucn-like peptide to thereby modulate CRF actions in mammals by means of direct or induced antagonistic(competitive) association with CRF receptors (CRF-Rs).

CRF-R is used to refer to a family of receptor protein subtypes which participate in the G-protein-coupled response of cells to CRF and Ucn-like ligands. CRF-Rs are coupled by heterotrimeric G-proteins to various intracellular enzymes, ion channels, and transporters. The G-proteins associate with the receptor proteins at the intracellular face of the plasma membrane. An agonist binding to a CRF-R catalyzes the exchanges of GTP for GDP on the α-subunit (G-protein "activation"), resulting in its dissociation and stimulation of one (or more) of the various signal-transducing enzymes and channels. G-protein preferentially stimulates particular effectors, and the specificity of signal transduction may be determined, therefore, by the specificity of G-protein/receptor interaction. CRF-R proteins mediate signal transduction through the modulation of adenylate cyclase and perhaps through PI turnover. For example, when CRF or Ucn binds to and activates the CRF-R, adenylate cyclase causes an elevation in the level of intracellular cAMP. An effective bioassay for evaluating whether a test compound is capable of elevating intracellular cAMP is carried out by culturing cells containing cDNA which expresses CRF receptor proteins in the presence of a potential agonist or antagonist whose ability to modulate signal transduction activity of CRF receptor protein is sought to be determined. Such transformed cells are monitored for either an increase or decrease in the level of intracellular cAMP which provides a determination of the effectiveness of the potential agonist or antagonist. Methods for measuring intracellular levels of cAMP, or measuring cyclase activity, are well known in the art.

A human CRF receptor was the first to be reported, and it was cloned from a human Cushing pituitary tumor as described in Chen R., et al, *P.N.A.S.*, 90, 8967–8971 (October 1993). It is referred to as hCRF-R1 or hCRF-RA and has 415 amino acids; a splice variant thereof includes an insert of 29-amino acids. A rat CRF receptor was isolated, approximately contemporaneously, by hybridization from a rat brain cDNA library. It is referred to as rCRF-R1; it has the 415 amino acid sequence which is set forth hereinafter as SEQ ID NO:10. It was disclosed in Perrin, M., et al., *Endocrinology*, 133, 3058–3061 (1993). It was found to be 97% identical at the amino acid level to the human CRF-R1, differing by only 12 amino acids. The receptor has since been reported to be widely distributed throughout the brain and the pituitary and to be likely present in the adrenals and spleen.

A second subclass of CRF receptors has more recently been found, and such receptors are arbitrarily referred to herein as CRF-R2 but are sometimes referred to as CRF-RB. One such receptor, having the amino acid sequence set forth hereinafter as SEQ ID NO:11, was obtained by the cloning and characterization of a cDNA from a mouse heart cDNA library. It is 431 amino acid residues in length, and the details of the receptor are set forth in Perrin, M., et al., *P.N.A.S*, 92, 2969–2973 (March 1995). It is hereinafter referred to as CRF-R2β, but has been referred to as CRF-RBL.

Another, slightly shorter receptor of this second subclass was independently obtained from a rat hypothalamus cDNA library. It is referred to herein as CRF-R2α and has the 411 amino acid residue sequence set forth hereinafter as SEQ ID NO:12. The details of its cloning are set forth in Lovenberg, T., et al., *P.N.A.S.*, 92, 836–840 (January 1995), wherein a second spliced variant was also identified via PCR as being a putative protein of 431 amino acids that would be the rat homolog of mCRF-R2β identified above. The 431 amino acid sequence is set forth hereinafter as SEQ ID NO:13 and can be seen to be homologous with mCRF-R2β. The distribution of Ucn throughout the rat brain is consistent with its being the endogenous ligand for CRF-R2, as is the fact that it exhibits a much higher binding affinity, than does CRF, for the receptor, particularly the R2s which is believed to be the main CRF-R in the brain.

Ucn-like peptides, including rUcn, hUcn and analogs thereof, can be easily synthesized as described in Example I hereinafter and then individually tested for binding affinity.

Binding affinity refers to the strength of interaction between ligand and receptor. To demonstrate binding affinity for a CRF receptor, the peptides of the invention are easily evaluated using a tracer ligand of known affinity, such as $^{125}$I-radiolabeled oCRF, in binding assay experiments which are well known in this art. The results of such assays indicate the affinity at which each Ucn-like ligand binds to a CRF receptor, expressed in terms of $K_i$, an inhibitory binding affinity constant relative to such a known standard. $K_i$ (inhibitory binding affinity constant) is determined using a "standard" or "tracer" radioactive ligand and thus measures the displacement of the tracer from the receptor or binding protein; it is most properly expressed with reference to such tracer. So long as these assays are carefully performed under specific conditions with relatively low concentrations of receptor or the like, the calculated $K_i$ will be substantially the same as its dissociation constant $K_D$. It is particularly efficient to test for $K_i$ because only a single tracer need be labelled, e.g. radioiodinated. Dissociation constant $K_D$ is representative of the concentration of ligand necessary to occupy one-half (50%) of the binding sites of a receptor or the like. A given ligand having a high binding affinity for a CRF receptor will require the presence of very little ligand to bind at least 50% of the available binding sites so that the $K_D$ value for that ligand and receptor will be a small number. On the other hand, a given ligand having a low binding affinity for a particular CRF receptor will require the presence of a relatively high level of the ligand to bind 50% of the sites, so that the $K_D$ value for that ligand and receptor will be a large number.

With respect to a particular receptor protein, a Ucn-like peptide having a $K_D$ of about 10 nM or less means that a concentration of the ligand (i.e., the Ucn-like peptide) of no greater than about 10 nM will be required to occupy at least 50% of the active binding sites of the receptor protein. Such values may be fairly determined from the results obtained using a radioiodinated standard and no more than approximately 0.8 nM of the receptor (approximately 10–20 pmol receptor/mg membrane protein). Preferred Ucn-like peptides have a binding affinity ($K_D$) such that a ligand concentration of about 10 nanomolar or less is required in order to occupy (or bind to) at least 50% of the receptor binding sites, and particularly preferred Ucn-like peptides have a binding affinity of 1 nM or less. Generally, a dissociation constant of about 5 nanomolar or lower is considered to be an indication of fairly strong affinity, and a $K_D$ of about 1 nanomolar or less is an indication of very strong affinity. For example, rUcn binds CRF-R1 with very strong affinity, having a $K_D$=about 0.18 nanomolar and binds CRF-R2β with similar strong affinity. It is also considered to be particularly advantageous to provide Ucn-like peptides which have a substantially higher affinity for CRF-R2, compared to CRF-R1, and which will thus be selective in their biological effect. Because CRF-R2 receptors are distributed widely throughout the body, Ucn will have a substantially greater effect than CRF in modulating many peripheral actions, and because the native peptide or fragments thereof should not be immunogenic, it should be a very good drug physiologically.

These binding assays employing CRF receptors are straightforward to perform and can be readily carried out with initially identified or synthesized peptides to determine whether such peptides are effective agonists of CRF, or alternatively to determine whether other shortened candidates are effective antagonists of CRF. Such binding assays can be carried out in a variety of ways as well known to one of skill in the art. A detailed example of such an assay is set forth in Perrin, M., et al., *Endocrinology*, 118, 1171–1179 (1986). Competitive binding assays employing Ucn are particularly contemplated to evaluate whether candidate peptides are effective agonists with respect to each of the receptors previously described, i.e. CRF-R1, CRF-R2β and CRF-R2α as well as assays with Ucn antagonists to determine whether candidates are effective antagonists. In such assays, Ucn can be appropriately labeled with a substance that is readily detected, such as a radioactive isotope, e.g. $^{125}$I, or an enzyme or some other suitable tag. For example, suitably labelled agonists, such as $^{125}$I-Tyr$^o$-Ucn, or suitably labelled antagonists, such as $^{125}$I-(cyclo 29–32)[D-Tyr$^{11}$, Glu$^{29}$, Lys$^{32}$]-Ucn(11–40), are particularly useful tracers for use in such receptor assays. Such receptor assays can be used as screens for potential drugs which interact with CRF and/or CRF receptors.

Very generally, the invention provides Ucn-like peptides, including Ucn and analogs of Ucn, having an amino acid sequence which is substantially the same as the following amino acid sequence based upon SEQ ID NO:8 and upon SEQ ID NO:15 (Formula I): Y-R$_1$-Pro-R$_4$-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$, wherein Y is an acyl group having 7 or less carbon atoms, preferably acetyl, or hydrogen; R$_1$ is Asp-Asp or Asp-Asn or Asp or Asn or desR$_1$; and R$_4$ is Pro or Ser; as well as nontoxic salts thereof. When the N-terminus is shortened by the deletion of 2 residues, it is preferably acylated, e.g. acetylated. These peptides have pharmacological properties somewhat similar to those of oCRF or r/hCRF and additional properties as described hereinafter. As indicated hereinbefore, analogs of the above having at least about 80% homology with the amino acid sequence of either hUcn or rUcn are preferred for the Ucn-like peptides of the invention, although peptides having at least 66% homology with either hUcn or rUcn, wherein all or all but one of the substitutions are conservative substitutions, are considered to be biologically active and to have advantages over known CRF peptides. Particularly preferred are analogs which are substantially the same as either hUcn or rUcn (as defined hereinbefore) and which have D-isomer amino acid substitutions and/or cyclizing bonds between the side chains of specific residues in the sequence which are known to increase ligand binding affinity for CRF receptors.

In addition to the foregoing general group of Ucn-like peptides, two additional groups are disclosed hereinafter based upon related syntheses and testing carried out in this general area with regard to ligands which bind to CRF-R.

The following group of analogs of Ucn does not merely include one or more conservative substitutions. Instead, bioactive Ucn analogs are found to be defined according to the following amino acid sequence: Y-Asp-R$_2$-Pro-R$_4$-Leu-Ser-Ile-Asp-Leu-Thr-D-Phe-His-Leu-Leu-Arg-Thr-Leu-Leu-R$_{19}$-Leu-Ala-Arg-Thr-Gln-Ser-Gln-Arg-Glu-R$_{29}$-Ala-Glu-R$_{32}$-Asn-Arg-Ile-R$_{36}$-Phe-R$_{38}$-Ser-Val-NH$_2$, wherein Y is an acyl group having 7 or less carbon atoms or hydrogen; R$_2$ is Asp or Asn; R$_4$ is Pro or Ser; R$_{19}$ is Glu or Ala; R$_{29}$ is Arg, Glu, Lys or Orn; R$_{32}$ is Gln, Lys, Orn or Glu; R$_{36}$ is Ile, C$^\alpha$MeIle or C$^\alpha$MeLeu; R$_{38}$ is Asp or Ala; provided that when R$_{29}$ is Glu, R$_{32}$ is either Lys or Orn and the side chains thereof are linked by an amide bond and that when R$_{32}$ is Glu, R$_{29}$ is either Lys or Orn and the side chains thereof are linked by an amide bond; and provided further that D-Phe$^{11}$ can be substituted by another D-isomer amino acid, preferably a D-isomer of a natural amino acid, such as D-Leu and more preferably one other than D-Cys; that Glu in the 31-position can be substituted by any D-amino acid, e.g. D-Glu, D-Asp, D-Arg, (imBzl)D-His, β-(2naphthyl)-D-Ala, etc., again preferably a D-isomer of a natural amino acid other than Cys; and that the N-terminus can be shortened by 1 or 2 residues. One particularly preferred Ucn analog is (cyclo 29–32)[Lys$^{29}$, D-Glu$^{31}$, Glu$^{32}$]-Ucn, with Ucn being either hUcn or rUcn; others are described in the Examples hereinafter. When N-terminally shortened by 7 to 10 residues, these Ucn analogs are effective antagonists.

Extensive synthesis and testing over the past 10+ years have shown that ligands for the CRF receptors can tolerate a number of changes in amino acid sequence of native r/hCRF which do not result in significant changes in bioactivity, such as would be indicative of the resulting analog being no longer able to bind and/or activate CRF receptors, particularly CRF-R1. As a result of this extensive earlier work, it has been found that one, two, or three substitutions can be made in the Ucn amino acid sequence, within certain limits as set forth hereinafter, that will result in Ucn analogs which retain the bioactivity of Ucn and, in some instances, may have even more desirable pharmacological characteristics.

Using the amino acid sequence of Ucn as a reference, these analogs should differ only by one, two or three substitutions from SEQ ID NO: 8 or from SEQ ID NO:15. The invention thus provides Ucn analogs according to the following amino acid sequence (SEQ ID NO: 14): Y-Xaa$_1$-Xaa$_2$-Pro-Xaa$_4$-Xaa$_5$-Ser-Xaa$_7$-Asp-Leu-Xaa$_{10}$-Xaa$_{11}$-Xaa$_{12}$-Xaa$_{13}$-Leu-Arg-Xaa$_{16}$-Xaa$_{17}$-Xaa$_{18}$-Xaa$_{19}$-Xaa$_{20}$-Xaa$_{21}$-Xaa$_{22}$-Xaa-$_{23}$-Xaa$_{24}$-Xaa$_{25}$-Xaa$_{26}$-Xaa$_{27}$-Xaa$_{28}$-Xaa$_{29}$-Ala-Xaa$_{31}$-Xaa$_{32}$-Asn-Arg-Xaa$_{35}$-Xaa$_{36}$-Xaa$_{37}$-Xaa$_{38}$-Xaa$_{39}$-Xaa$_{40}$-NH$_2$, wherein Y is an acyl group having 7 or less carbon atoms or hydrogen; Xaa$_1$ is Asp, Glu or Gln; Xaa$_2$ is Asn, Asp, Glu or Gly; Xaa$_4$ is Ser or Pro; Xaa$_5$ is Leu, Ile or Met; Xaa$_7$ is Ile or Leu; Xaa$_{10}$ is Thr or Ser; Xaa$_{11}$ is Phe or Leu; Xaa$_{12}$ is His or Glu; Xaa$_{13}$ is Leu or Met; Xaa$_{16}$ is Thr, Asn, Glu, or Lys; Xaa$_{17}$ is Leu, Met or Val; Xaa$_{18}$ is Leu or Ile; Xaa$_{19}$ is Glu or His; Xaa$_{20}$ is Leu, Met, Ile or Arg; Xaa$_{21}$ is Ala, Glu or Thr; Xaa$_{22}$ is Arg or Lys; Xaa$_{23}$ is any natural amino acid and preferably Thr, Ser, Ala, Ile, Met, Val, Asn, Gln, Gly, Lys, His, Leu, Glu or Asp; Xaa$_{24}$ is Gln, Glu or Asp; Xaa$_{25}$ is any natural amino acid and preferably Ser, Thr, Ala, Ile, Met, Val, Asn, Gln, Gly, Lys, His, Leu, Glu or Asp; Xaa$_{26}$ is Gln, Leu or Glu; Xaa$_{27}$ is Arg, Ala or Lys; Xaa$_{28}$ is Glu or Gln; Xaa$_{29}$ is Arg or Gln; Xaa$_{31}$ is any natural amino acid and preferably Ala, Ile, Met, Val, Asn, Gln, Gly, Lys, His, Leu, Glu or Asp; Xaa$_{32}$ is any natural amino acid and preferably Ala, Ile, Met, Val, Asn, Gln, Gly, Lys, His, Leu, Glu or Asp; Xaa$_{35}$ is Ile, Lys, Leu or Asn; Xaa$_{36}$ is Ile, Tyr, Met or Leu; Xaa$_{37}$ is Phe, Leu or Met; Xaa$_{38}$ is Asp or Glu; Xaa$_{39}$ is Ser, Ile, Glu or Thr; and Xaa$_{40}$ is Val, Ile, Phe or Ala; provided that there are no more than 3 residues different from the hUcn or the rUcn amino acid sequence and that the N-terminus may be shortened by 1 or 2 residues. Moreover, these Ucn analogs when N-terminally shortened by 7 to 10 residues constitute effective antagonists.

The Ucn-like peptides of the invention may be chemically synthesized by any suitable method, such as by exclusively solid-phase techniques, by partial solid-phase techniques, by fragment condensation or by classical solution addition.

Ucn may also be synthesized by recombinant DNA techniques as may its analogs which include only natural amino acids. The amino acid sequence for rUcn (SEQ ID NO:8) was deduced from a partial cDNA clone isolated from a rat brain cDNA library. Set forth in Table 2 hereinafter is the native rat nucleic acid sequence encoding Ucn (SEQ ID NO:9). The additional codon encoding glycine that is present at the end of the native sequence is expected to account for the C-terminal amidation of rUcn.

TABLE 2

```
GAC GAC CCG CCG TTG TCC ATC GAC CTC ACC TTC CAC CTG CTG CGG ACC
Asp Asp Pro Pro Leu Ser Ile Asp Leu Thr Phe His Leu Leu Arg Thr
 1               5                   10                  15

CTG CTA GAG CTA GCT CGG ACA CAG AGC CAG CGC GAG CGC GCA GAG CAG
Leu Leu Glu Leu Ala Arg Thr Gln Ser Gln Arg Glu Arg Ala Glu Gln
             20                  25                  30

AAC CGC ATC ATA TTC GAT TCG GTG GGCAAGTGA
Asn Arg Ile Ile Phe Asp Ser Val
             35              40
```

Using the nucleic acid encoding rUcn as a probe, the nucleic acid encoding the mature hUcn was isolated from a human genomic placental library. Set forth in TABLE 2A hereinafter is the portion of native human nucleic acid sequence encoding the mature Ucn peptide (see SEQ ID NO:16), with the additional codon for glycine at the end being expected to account for C-terminal amidation.

TABLE 2A

```
GAC AAC CCT TCT GTC TCC ATT GAC CTC ACC TTT CAC CTG CTG CGG ACC
Asp Asn Pro Ser Leu Ser Ile Asp Leu Thr Phe His Leu Leu Arg Thr
 1               5                   10                  15

CTG CTG GAG CTG GCG CGG ACG CAG AGC CAG CGG GAG CGC GCC GAG CAG
Leu Leu Glu Leu Ala Arg Thr Gln Ser Gln Arg Glu Arg Ala Glu Gln
             20                  25                  30

AAC CGC ATC ATA TTC GAC TCG GTG GGCAAGTGA
Asn Arg Ile Ile Phe Asp Ser Val
             35              40
```

Synthesis by the use of recombinant DNA techniques, for purposes of this application, should be understood to include the suitable employment isolated nucleic acid encoding for Ucn or an appropriate analog, as is well known in the art at the present time. As explained in detail hereinafter, synthetic Ucn peptides may be obtained by transforming a microorganism using an expression vector including appropriate regulatory sequences associated with nucleic acid encoding a Ucn-like peptide and causing such transformed microorganism to express the Ucn peptide.

Because of the relative shortness of the Ucn-like peptides, about 40 residues or less, chemical or chain elongation synthesis is presently felt to be the method of choice. Analogs of hUcn or rUcn having one or more substitutions can be readily synthesized in this manner and then tested for biological activity in a straightforward manner to determine the specific biological effect of such substitution(s). Common to such chemical syntheses of peptides is the protection of the labile side chain groups of the various amino acid moieties with suitable protecting groups which will prevent a chemical reaction from occurring at that site until the group is ultimately removed. Also common is the protection of an alpha-amino group on an amino acid or a short peptide fragment while that entity reacts at the free carboxyl group to effect chain elongation, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

Thus, in such chemical syntheses, intermediates are formed having a protected amino acid sequence such as the following which is based on hUcn SEQ ID NO:15 (Formula II): $X^1$-Asp($X^5$)-Asn($X^4$) -Pro-Ser($X^2$) -Leu-Ser($X^2$)-Ile-Asp($X^5$)-Leu-Thr($X^2$)-Phe-His($X^6$)-Leu-Leu-Arg($X^3$)-Thr ($X^2$)-Leu-Leu-Glu($X^5$)-Leu-Ala-Arg($X^3$)-Thr ($X^2$)-Gln ($X^4$)-Ser($X^2$)-Gln ($X^4$)-Arg($X^3$)-Glu($X^5$)-Arg ($X^3$)-Ala-Glu ($X^5$)-Gln($X^4$)-Asn($X^4$)-Arg($X^3$)-Ile-Ile-Phe-Asp($X^5$)-Ser ($X^2$)-Val-$X^7$ (or suitably N-terminally shortened versions thereof) wherein:

$X^1$ is either hydrogen or an alpha-amino protecting group. The alpha-amino protecting groups contemplated by $X^1$ are those known to be useful in the art in the step-wise synthesis of polypeptides. Among the classes of alpha-amino protecting groups covered by $X^1$ are (1) acyl-type protecting groups, such as formyl, acrylyl(Acr), benzoyl(Bz) and acetyl (Ac) which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as fluorenylmethyloxycarbonyl(FMOC), cyclopentyloxycarbonyl, adamantyloxycarbonyl,and cyclohexyloxycarbonyl; and (5) thiourethan-type protecting groups, such as phenylthiocarbonyl. The preferred alpha-amino protecting group is BOC if the synthesis employs acid-catalyzed removal of the alpha-amino protecting groups; however, for syntheses employing a base-catalyzed removal strategy, FMOC is preferred, in which case, more acid-labile side chain protecting groups can be used, including t-Butyl esters or ethers as well as BOC.

$X^2$ is hydrogen or a protecting group for the hydroxyl group of Thr and Ser and is preferably acetyl(Ac), benzoyl (Bz), tert-butyl, triphenylmethyl(trityl), tetrahydropyranyl, benzyl ether(Bzl) or 2,6-dichlorobenzyl (DCB). The most preferred protecting group is Bzl.

$X^3$ is hydrogen or a protecting group for the guanidino group of Arg, preferably selected from nitro, p-toluenesulfonyl(Tos), Z, adamantyloxycarbonyl and BOC. Tos is preferred for a BOC strategy, and 4-methoxy-2,3,6-trimethyl benzenesulfonyl (MTR) or pentamethyl chroman-6-sulfonyl (PMC) is preferred for FMOC strategies.

$X^4$ is hydrogen or a protecting group for the side chain amido group of Asn or Gln, preferably xanthyl (Xan). Asn or Gln is preferably coupled without side chain protection in the presence of hydroxybenzotriazole (HOBt).

$X^5$ is hydrogen or an ester-forming protecting group for the β- or γ-carboxyl group of Asp or Glu, preferably cyclohexyl (OChx), benzyl (OBzl), 2,6-dichlorobenzyl, methyl, ethyl and t-butyl ester (Ot-Bu). Chx is preferred for a BOC strategy and Ot-Bu for FMOC strategy.

$X^6$ is hydrogen or a protecting group for the side chain imidazole nitrogen of His, such as Tos.

The selection of a side chain amino protecting group is not critical except that the protecting group should be one which is not removed during deprotection of the alpha-amino groups during the synthesis. Hence, the alpha-amino protecting group and the side-chain-amino protecting group cannot be the same.

$X^7$ is $NH_2$, a protecting group, such as an ester, or is an anchoring bond of the type used in solid phase synthesis for linking the peptide being synthesized to a solid resin support, preferably one represented by the formulae:

—NH-benzhydrylamine (BHA) resin support and

—NH-paramethylbenzhydrylamine (MBHA) resin support.

Cleavage from a BHA or MBHA resin directly gives the Ucn-like peptide in amidated form. By employing a methyl-derivative of such a resin, if desired, the corresponding, equivalent, methyl-substituted amide can be created. Alternatively, using an appropriate resin support, the ethylamide, which is also considered to be an equivalent, can be created as well known in this art.

In the formula for the intermediate, at least one of $X^1$, $X^2$, $X^3$, $X^4$, $X^5$ and $X^6$ is a protecting group. In selecting a particular side chain protecting group to be used in the synthesis of the peptides, the following rules are followed: (a) the protecting group should be stable to the reagent, and under the reaction conditions, selected for removing the alpha-amino protecting group at each step of the synthesis, (b) the protecting group should retain its protecting properties and not be split off under coupling conditions and (c) the protecting group must be removable upon completion of the synthesis under reaction conditions that will not alter the peptide chain.

For the acyl group at the N-terminus of a Ucn-like agonist peptide, which is represented by Y, acetyl, formyl, acrylyl and benzoyl are preferred. Moreover, as indicated earlier, the N-terminus can be slightly shortened by removal of the N-terminal residue or the first two N-terminal residues without significantly affecting biological potency of the peptide to function as a Ucn agonist, and when such shortening occurs, acylation of the residue at the shortened N-terminus may be preferred. More extensive shortening of the N-terminus by a sequence of 7 to 11 residues results in the creation of Ucn antagonists which strongly bind CRF-R without activating the receptor as discussed hereinafter.

Overall, there is broadly provided a process for the manufacture of peptides defined by Formula I or analogs thereof comprising (a) forming an intermediate peptide according to Formula II or an analog thereof wherein there is at least one protective group, with $X^1$, $X^2$, $X^3$, $X^4$, $X^5$ and $X^6$ being each either hydrogen or a protective group, and $X^7$ being either a protective group or an anchoring bond to resin support or $NH_2$ and (b) splitting off the protective group or groups or anchoring bond from the intermediate peptide of the Formula II and (c) if desired, converting the resulting peptide into a nontoxic salt thereof.

When the peptides of the invention are prepared by chemical synthesis, they are preferably prepared using solid phase synthesis, such as that described by Merrifield, *J. Am. Chem. Soc.*, 85, p 2149 (1964), although other equivalent chemical syntheses known in the art can also be used as previously mentioned. Thus, Ucn-like peptides can be prepared in a straightforward manner and then simply tested for biological activity. This facilitates the ready preparation and evaluation of Ucn-like peptides which are analogs of hUcn or rUcn. Solid-phase synthesis is preferably commenced from the C-terminus of the peptide by coupling a protected alpha-amino acid to a suitable resin as generally set forth in U.S. Pat. No. 4,244,946 issued Jan. 21, 1981 to Rivier et al. by coupling with the free carboxyl group. The synthesis of Ucn can be initiated by coupling alpha-amino-protected Val to a BHA resin using methylene chloride and dimethylformamide (DMF). Following the coupling of BOC-Val to the resin support, the alpha-amino protecting group may be removed using trifluoroacetic acid(TFA) in methylene chloride, TFA alone or with HCl in dioxane. Preferably 50 volume % TFA in methylene chloride is used with 0–5 weight % 1,2 ethanedithiol. The deprotection is carried out at a temperature between about 0° C. and room temperature. Other standard cleaving reagents and conditions for removal of specific alpha-amino protecting groups may be used as described in Schroder & Lubke, "The Peptides", 1, pp 72–75 (Academic Press 1965).

After removal of the alpha-amino protecting group of Val, the remaining alpha-amino- and side chain-protected amino acids are coupled stepwise in the desired order to obtain the intermediate compound of Formula II. As an alternative to adding each amino acid separately in the synthesis, some of them may be coupled to one another prior to addition to the solid phase reactor. The selection of an appropriate coupling reagent is within the skill of the art. Particularly suitable as coupling reagents are N,N'-dicyclohexyl carbodiimide (DCCI) and N,N'-diisopropyl carbodiimide (DICI).

Activating reagents used in the solid phase synthesis of the peptides of the invention are well known in the peptide art. Examples of suitable activating reagents are carbodiimides, such as N,N'-diisopropyl carbodiimide and N-ethyl-N'-(3-dimethylaminopropyl) carbodiimide. Other activating reagents and their use in peptide coupling are described by Schroder & Lubke, supra, in Chapter III and by Kapoor, *J. Phar. Sci.*, 59, pp 1–27 (1970). P-nitrophenyl ester (ONp) may also be used to activate the carboxyl end of Asn or Gln for coupling. For example, BOC-Asn (ONp) can be coupled overnight using one equivalent of HOBt in a 50% mixture of DMF and methylene chloride, in which case no DCCI is added.

Each protected amino acid or amino acid sequence is introduced into the solid phase reactor in about a fourfold excess, and the coupling is carried out in a medium of dimethylformamide (DMF):$CH_2Cl_2$ (1:1) or in DMF or $CH_2Cl_2$ alone. In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the alpha-amino protecting group prior to the coupling of the next amino acid. The coupling reactions can be performed automatically, as on a Beckman 990 automatic synthesizer, using a program such as that reported in Rivier et al., *Biopolymers*, 1978, 17, pp.1927–1938.

After the desired amino acid sequence has been completed, the intermediate peptide is removed from the resin support by treatment with a suitable clearing agent, such as liquid hydrogen fluoride, which not only cleaves the peptide from the resin but also cleaves all remaining side chain protecting groups $X^2$, $X^3$, $X^4$, $X^5$ and $X^6$ and the alpha-amino protecting group $X^1$ (unless it is an acyl group which is intended to be present in the final peptide). When using hydrogen fluoride for cleaving, anisole or cresole and methylethyl sulfide are preferably included in the reaction vessel as scavengers. The BOC protecting group at the N-terminus is preferably cleaved with trifluoroacetic acid (TFA)/ethanedithiol prior to the cleaving of the peptide from the resin.

The determination of whether any Ucn-like peptide of about 40 residues in length, or a fragment thereof, or an antagonist version thereof, will have desirable pharmacological properties can be made in a straightforward manner. First, assays are run to determine the effect of a candidate agonist or antagonist peptide on the different CRF receptors; then, the ability of the peptide to promote or inhibit production of ACTH is determined. Fragments which function as CRF-BP blockers can be likewise similarly assayed using an inhibitory binding assay with hCRF-BP and a known labelled ligand.

The candidate peptide is easily evaluated in binding assays with the various CRF receptors earlier discussed using assays as described in Perrin, M., et al., *Endocrinology*, 118, 1171–1179 (1986). A binding assay with human CRF-R1 is preferably carried out using a radioligand oCRF analog; such a binding assay utilizing CRF-R1 receptor is described in Chen, et al., *P.N.A.S.*, 90, supra.

A straightforward assay using rat anterior pituitary cells in monolayer culture can be carried out to determine whether a candidate peptide thereof will function as a CRF agonist and stimulate ACTH secretion by activating CRF receptors on such cells. The procedure which is used is that generally set forth in *Endocrinology*, 91, supra. A very similar assay is used to test for antagonistic properties, using a challenge dose of oCRF or the like.

By the in vivo administration to mammals of peptides which have a high affinity to human CRF binding protein and which thus compete with endogenous CRF and Ucn for binding to hCRF-BP, CRF-BP is effectively blocked. This leaves endogenous CRF and Ucn available in higher concentrations to carry out their usual biological functions throughout the body, particularly in localized areas where the peptide is administered and/or where CRF-BP is present.

More specifically, fragments of Ucn, or analogs of Ucn, between about 19 and 28 residues in length have a very high affinity to hCRF-BP, but generally exhibit relatively low propensity for binding CRF receptors. As a result, these blocking fragments can be administered to prevent the clearance of endogenous CRF and/or Ucn from particular regions in the body and thereby stimulate the biological effect of CRF and/or Ucn in vivo. In certain instances, it may be advantageous to administer such peptides along with CRF or Ucn or an agonist thereof. The very nature of these fragments is such that potentially undesirable immunogenic side effects are minimized or totally obviated. They might also be administered along with antagonists to prevent the clearance of antagonists having a fairly high binding affinity to hCRF-BP from a target region. These blocking fragments are useful for therapeutic treatment to promote parturition in pregnancy, to stimulate the respiratory system, to combat obesity, and to counteract the effects of Alzheimer's disease, and of chronic fatigue syndrome; for the latter four indications, the blocking fragments are preferably administered in a manner so as to be delivered to the brain.

Ucn peptides can be used in diagnostic methods to detect the level of Ucn present in a body sample as well as in an inoculum for the preparation of antibodies that immunoreact with epitopes on Ucn. Antibodies generated against Ucn can be employed for diagnostic applications, therapeutic applications, and the like. Such antibodies can be prepared employing standard techniques, as are well known to those of skill in the art, using Ucn or a fragment thereof, as an antigen. Antibodies of the present invention are typically produced by immunizing a mammal, e.g. rabbit, sheep, goat, etc., with an inoculum containing Ucn or fragment thereof thereby inducing the production of antibody molecules having immunospecificity for the immunizing agent.

Antibodies which recognize Ucn are raised against either the entire 40-residue amino acid sequence or against a synthetic fragment of a sequence of at least about 5 or preferably 6 residues. For example, such antibodies can be raised against the 6 N-terminal residues, or against the 6 C-terminal residues, or against an interior sequence, such as the sequence embracing residues 18–23. Such antibodies will bind to and thus can be employed to indicate the presence of Ucn; they are therefore useful in assays. Moreover, certain of these antibodies will bind to and biologically inactivate Ucn, and such antibodies can be administered to animals for the purpose of neutralizing endogenous Ucn. In an instance where endogenous antibodies are being created that would bind Ucn, short amino acid sequences from Ucn might be administered as antibody blockers. To generate such blocking antibodies, either the entire 40-residue sequence can be used, or a short peptide sequence can be synthesized constituting one region of particular interest. Such a synthetic short chain peptide is generally conjugated to a large carrier molecule, and the conjugate is then used as inoculum to induce a mammalian immune system in rabbits or sheep or the like. Details of the production of such polyclonal antibodies are set forth in U.S. Pat. No. 4,864,019 (Sep. 5, 1989). If instead of polyclonal antibodies, it is desired to produce monoclonal antibodies, such can be made in a straightforward manner using similar inoculum by employing hybridoma techniques now well established in this art. Details of exemplary monoclonal antibody production are set forth in U.S. Pat. No. 5,032,521 (Jul. 16, 1991), and U.S. Pat. No. 5,051,364 (Sep. 24, 1991).

Antibodies so produced can be used in diagnostic methods and systems to detect the level of Ucn present in a human or other mammalian body sample, such as tissue or fluid. The anti-Ucn antibodies may also be used for immunoaffinity or affinity chromatography purification of Ucn, the details of which are well known in this art. In addition, an anti-Ucn antibody can be used in human therapeutic methods. Moreover, it is contemplated that DNA encoding such antibodies may be injected via gene therapy methods to raise desired antibodies within a patient or alternatively to provide antibody blockers in an appropriate situation.

The lack of evolutionary digression with respect to the amino acid sequences of the 41-residue CRF biological messenger in rats and humans (which sequences are identical) is fairly indicative of the probability of conserved regions in the corresponding amino acid sequences of Ucn in mammalian species, such as human, bovine, porcine, ovine, caprine, murine, canine, feline, baboon, monkey, rabbit, etc. The corollary is that, once one has a significant portion of the Ucn nucleic acid sequence of one mammalian species, i.e. the rat sequence as disclosed herein, it is a straightforward exercise to obtain naturally occurring variant homolog nucleic acid sequences of other animal species which encode homologs, such as CRF-binding proteins (see e.g., Potter et al., *Nature*, 349, 423–426 (1991), where it was shown that the cDNA coding region for human serum-derived CRF binding protein was of sufficient homology in the rat cDNA coding region to permit identification of the latter. The first disclosed nucleic acid sequence (SEQ ID NO: 9) is of the native rat species; in addition to its being useful in an expression vector to express a Ucn peptide, it is also useful to obtain the DNA of other mammalian species encoding the respective counterpart Ucn peptides. In this respect, either the entire nucleic acid sequence or nucleic acid sequences at least about 14 nucleotides in length can be used as hybridization probes to obtain and clone counterpart mammalian sequences, as is presently well known in this art. Similarly, primers based upon the foregoing nucleic acid sequence can be used along with PCR (Polymerase Chain Reaction) techniques to amplify nucleic acid sequences of other mammalian species using suitable sources of DNA.

As used herein, a nucleic acid "probe" may be a single-stranded DNA or RNA that has a nucleotide sequence of at least 14, and preferably at least 20 or more, contiguous bases that are the same as (or the complement of) any 14 or more contiguous bases set forth in SEQ ID NO:9.

Labeled nucleic acid encoding Ucn, or fragments thereof, can be employed to probe cDNA libraries, genomic libraries and the like for additional nucleotide sequences encoding other novel mammalian members of the Ucn family. Such screening may be initially carried out under stringency conditions employing a temperature of about 42.5° C., a formamide concentration of about 20%, and a salt concentration of about 5× standard saline citrate (SSC; 20×SSC contains 3M sodium chloride, 0.3M sodium citrate, pH 7.5). Such conditions will allow the identification of sequences having substantial similarity with the probe sequence, without requiring perfect homology. By "substantial similarity" is meant nucleotide sequences which share at least about 50% homology. It may be desirable to select hybridization conditions which will identify only sequences having at least 70% homology with the probe, while discriminating against sequences which have a lower degree of homology with the probe; such is effected by increasing the stringency used to exceed the above-stated conditions as is well known in this art.

For example, using established methods well known to those skilled in the art (see e.g., *Molecular Cloning, A Laboratory Manual* 2Ed, Chapter 8, Construction and Analysis of cDNA Libraries, J. Sambrook et al. (1989)), either the entire SEQ ID NO:9 or portions thereof of at least about 14 or 17 or 20 nucleotides in length may be used to screen mammalian genomic or cDNA libraries to identify and isolate homologous nucleic acids encoding Ucn from human and other mammalian species. Oligonucleotide sequences of about 14 or 17 or 20 nucleotides or longer can be prepared by conventional in vitro synthesis techniques. Screening with such oligonucleotides as probes is preferably carried out under high stringency conditions as defined in Sambrook et al., supra, Chapter 11, pp. 11.45–11.57.

As indicated above, possession of a native DNA sequence encoding a specific peptide hormone of one mammalian species allows one to obtain the homologous DNA sequence of other mammalian species. Isolation of nucleotide sequences encoding Ucn peptides of other species often involves utilization of either a genomic library or a cDNA library made from RNA isolated from tissue containing Ucn. If such a source is available, it will generally be preferable to create a cDNA library for isolation of nucleotide sequences encoding Ucn so as to avoid any possible problems arising from attempts to determine intron/exon borders. Libraries can be made in either eukaryotic or prokaryotic host cells. Widely available cloning vectors, such as plasmids, cosmids, phage and the like, can be used to generate genetic libraries suitable for the isolation of nucleotide sequences encoding Ucn peptides.

Methods for screening genetic libraries for the presence of target nucleotide sequences include using such probes based on the sequence of a known nucleotide sequence are described in detail in Chapter 11 of Sambrook et al., supra. In the present situation, it may be preferable to use the entire length of the rat nucleotide sequence SEQ ID NO:9 labeled with radionuclides, enzymes, biotin, fluoresces, or the like, as a probe for screening such genetic libraries.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-nucleic acid can be readily varied by those of skill in the art. As used herein, the phrase "high stringency" hybridization refers to conditions that permit target-nucleic acid to bind a complementary nucleic acid that has at least about 80% homology to the target-nucleic acid. An example of such stringency conditions would be conditions that are minimally equivalent to hybridization in 50% formamide, 5×Denhart's solution, 5×SSPE, 0.2% SDS at 42° C., followed by washing in 0.2×SSPE, 0.2% SDS, at 65° C. Denhart's solution and STPE are desirable in Sambrook et al., *Molecular Cloning, A Laboratory Manual,* Cold Spring Harbor Laboratory Press (1989) and are well known to those of skill in this art; there are other suitable hybridization buffers that may be used. It may be preferred to use stringency conditions requiring greater than about 90% homology to target-DNA.

As an example, the human form of Ucn was successfully cloned from a human placental genomic library. Approximately $0.6 \times 10^6$ phage plaques of a human placental genomic library in the EMBL3 SP6/T7 vector (Clontech) were screened by hybridization using a probe corresponding to the mature peptide region of rat Ucn. The 160 bp probe encoding the rat Ucn mature peptide was synthesized by PCR using the following oligos (sense: 5'-TGCAGGCGAGCGGCAACGACGAGACGA-3') (SEQ ID NO:18) and (antisense: 5'-TACGGGGCCGATCACTT-GCCCACCGAG-3') SEQ ID NO:19) and [$\alpha^{32}$P-dCTP]. Hybridization was carried out at 42° C. in standard buffers with 20% formamide. Final washes were at 42° C. in 2×SSC/0.1% SDS. The phage DNA from an individual positive plaque for the clone was purified and then subcloned into pBluescript (Strategene). Dideoxy sequencing was done using the Sequenase kit (US Biochemical).

The genomic clone isolated from the library which contains the gene for human Ucn has an insert size of approximately 15 kb. A large number of base pairs of the insert have been sequenced (see SEQ ID NO:16) in the region corresponding to the precursor and the mature peptide region of human Ucn. The portion of nucleotide sequence initially sequenced encoding the mature human Ucn peptide, as compared to the mature rat Ucn peptide, was set forth in TABLE 2A hereinbefore. The nucleotide sequence for the mature human Ucn peptide is 88% similar to the nucleotide sequence for the rat Ucn peptide. The amino acid sequence encoded by this region shows 95% similarity between human Ucn and rat Ucn. The mature human peptide (see residues 83–122 of SEQ ID NO:15) is 40 residues of the total of 124.

Another suitable technique which may be used in the present situation involves the use of primers based on sequences derived from rat Ucn nucleic acid and the polymerase chain reaction (PCR) to amplify target nucleic acid. The target can then be isolated using a specific hybridization probe based on the amplified segment, which is then analyzed for its overall sequence and the polypeptide which it encodes.

To synthesize a peptide of the invention by recombinant DNA, a double-stranded DNA which encodes the desired peptide can be synthetically constructed. Although PCR techniques might nowadays be the method of choice to produce a DNA sequence, for example, SEQ ID NO:9, DNA encoding Ucn can be designed using certain codons that are particularly efficient for polypeptide expression in a certain organism, i.e. selection might employ those codons which are most efficient for expression in the type of organism which is to serve as the host for the recombinant vector. However, any correct set of codons will encode a desired product, although perhaps slightly less efficiently. Codon selection may also depend upon vector construction considerations; for example, it may be necessary to avoid placing a particular restriction site in the DNA coding sequence if, subsequent to inserting the coding sequence, the vector is to be manipulated using a restriction enzyme that cleaves at such a site. Of course one would avoid placing restriction sites in the DNA coding sequence if the host organism, which is to be transformed with the recombinant vector, is known to produce a restriction enzyme that would cleave at such a site within the DNA chain.

Isolated nucleotide sequences encoding Ucn and analogs thereof can be used to produce purified Ucn by either recombinant DNA methodology or by in vitro polypeptide synthesis techniques. The term "isolated" refers to a nucleotide sequence or a polypeptide sequence that has been manually produced and is separated from its native, in vivo, cellular environment and is present in the substantial absence of other biological molecules of the same type. As a result of this human intervention, the recombinant, isolated and/or substantially pure DNAs, RNAs, polypeptides and proteins of the invention can be produced in large quantities and are useful in ways that the DNAs, RNAs, polypeptides or proteins as they naturally occur are not, such as identification of selective drugs or compounds. The term "purified" as used herein for nucleotide sequences preferably means at least 95% by weight, and most preferably at least 99% by weight, of biological macromolecules of the same type present (but water, buffers, and other small molecules, can be present).

To assemble a synthetic, nonchromosomal nucleic acid sequence, oligonucleotides are constructed by conventional procedures such as those described in Sambrook et al., supra. Sense and antisense oligonucleotide chains, up to about 70 nucleotide residues long, are synthesized, preferably on automated synthesizers well known in this art. The oligonucleotide chains are constructed so that portions of the sense and antisense oligonucleotides overlap, associating with each other through hydrogen bonding between complementary base pairs and thereby forming double-stranded chains, in most cases with gaps in the strands. Subsequently, the gaps in the strands are filled in, and oligonucleotides of each strand are joined end to end with nucleotide triphosphates in the presence of appropriate DNA polymerases and/or with ligases. As an alternative to such stepwise construction of a synthetic nucleic acid sequence, DNA or cDNA encoding the complete structure of a native polypeptide as obtained by screening a library is used. As indicated hereinbefore, amplification is preferably carried out by using PCR, and the isolated and purified DNA is then incorporated into recombinant molecules.

The desired nucleic acid coding sequence to be inserted into a vector preferably has linkers at its ends to facilitate insertion into restriction sites within the cloning vector. Optionally, the nucleic acid coding sequence may be constructed so as to encode the desired peptide as a portion of a fusion polypeptide; and if so, the coding sequence will generally contain terminal sequences that encode amino acid residue sequences that serve as proteolytic processing sites, whereby the encoded polypeptide may be proteolytically cleaved from the remainder of the fusion polypeptide. The terminal portions of the nucleic acid coding sequence may also contain appropriate start and stop signals.

The desired peptide is then expressed by recombinant techniques after the nucleic acid coding sequence is functionally inserted into a vector. By "functionally inserted" is meant in proper reading frame and orientation, as is well understood by those skilled in this art. For example, when producing a genetic construction containing a complete Ucn reading frame, the preferred starting material is a cDNA library isolate encoding Ucn rather than a genomic library isolate. Typically, the Ucn-encoding sequence will be inserted downstream from a promoter and will be followed by a stop codon, although production as a hybrid protein followed by cleavage may be used, if desired. In general, host-cell-specific sequences which improve the production yield of Ucn will be used, and appropriate control sequences will be added to the expression vector, such as enhancer sequences, polyadenylation sequences, and ribosome binding sites.

The production of Ucn can be carried out in both prokaryotic and eukaryotic cell lines to provide protein for biological and therapeutic use. While Ucn synthesis is easily demonstrated using either bacteria or yeast cell lines, the synthetic genes should also be insertable for expression in cells of higher animals, such as Chinese hamster ovary (CHO) cells or mammalian tumor cells as described in detail in Sambrook et al, supra. Some mammalian cells may be grown, for example, as peritoneal tumors in host animals, and Ucn harvested from the peritoneal fluid. Descriptions of mammalian expression systems, baculovirus expression systems, bacterial expression systems and yeast expression systems are set forth in U.S. Pat. No. 5,212,074 (May 18, 1993).

The following Examples set forth preferred chemical methods for synthesizing Ucn, Ucn analogs, Ucn fragments, and Ucn antagonists, by the solid-phase chain elongation technique.

EXAMPLE I

The synthesis of rat Ucn having the formula (SEQ ID NO:8):
Asp-Pro-Pro-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ is conducted in a stepwise manner on a MBHA hydrochloride resin, such as available from Bachem, Inc., having a substitution range of about 0.1 to 0.5 mmoles/gm. resin. The synthesis is performed on an automatic Beckman 990B peptide synthesizer using a suitable program, such as the following:

| STEP | REAGENTS AND OPERATIONS | MIX TIMES MIN. |
|---|---|---|
| 1 | CH$_2$Cl$_2$ wash-80 ml. (2 times) | 3 |
| 2 | Methanol (MeOH) wash-30 ml. (2 times) | 3 |
| 3 | CH$_2$Cl$_2$ wash-80 ml. (3 times) | 3 |
| 4 | 50 percent TFA plus 5 percent 1,2-ethanedithiol in CH$_2$Cl$_2$-70 ml. (2 times) | 12 |
| 5 | Isopropanol wash-80 ml. (2 times) | 3 |
| 6 | TEA 12.5 percent in CH$_2$Cl$_2$-70 ml. (2 times) | 5 |
| 7 | MeOH wash-40 ml. (2 times) | 2 |
| 8 | CH$_2$Cl$_2$ wash-80 ml. (3 times) | 3 |

Coupling of BOC-Val results in the substitution of about 0.35 mmol Val per gram of resin. All solvents that are used are carefully degassed, preferably by sparging with an inert gas, e.g. helium or nitrogen, to insure the absence of oxygen.

After deprotection and neutralization, the peptide chain is built step-by-step on the resin. Generally, one to two mmol. of BOC-protected amino acid in methylene chloride is used per gram of resin, plus one equivalent of 2 molar DCCI in methylene chloride, for two hours for the coupling of each additional residue. When BOC-Arg(Tos) is being coupled, a mixture of 50% DMF and methylene chloride is used. Bzl is used as the hydroxyl side-chain protecting group for Ser and Thr. The amido group of Asn or Gln can be protected by Xan but need not be. BOC-Asn or BOC-Gln is coupled overnight using one equivalent of DCC and two equivalents of HOBt in a 50% mixture of DMF and methylene chloride. Tos is used to protect the guanidino group of Arg and the imidazole nitrogen of His. The side chain carboxyl group of Glu or Asp is protected by OChx. At the end of the synthesis, the following composition is obtained:
BOC-Asp(OChx)-Asp(OChx)-Pro-Pro-Leu-Ser(Bzl)-Ile-Asp(OChx)-Leu-Thr(Bzl)-Phe-His(Tos)-Leu-Leu-Arg(Tos)-Thr(Bzl)-Leu-Leu-Glu(OChx)-Leu-Ala-Arg(Tos)-Thr(Bzl)-Gln-Ser(Bzl)-Gln-Arg(Tos)-Glu(OChx)-Arg(Tos)-Ala-Glu(OChx)-Gln-Asn-Arg(Tos)-Ile-Ile-Phe-Asp(OChx)-Ser(Bzl)-Val-NH-resin support.

In order to cleave and deprotect the resulting peptide, the peptide-resin is treated with 1.5 ml. anisole, 0.5 ml. of methylethylsulfide and 15 ml. hydrogen fluoride (HF) per gram of peptide-resin, first at −20° C. for 20 min. and then at 0° C. for one and one-half hours. After elimination of HF under high vacuum, the resin-peptide is washed with dry diethyl ether, and the peptide amide is then extracted with de-gassed 2N aqueous acetic acid or a 1:1 mixture of acetonitrile and water. The extract is separated from the resin by filtration, and then lyophilized.

The lyophilized peptide amide is purified by preparative or semi-preparative HPLC as described in Rivier et al., *J. Chromatography*, 288, 303–328 (1984); and Hoeger et al., Biochromatography, 2, 3, 134–142 (1987). The chromatographic fractions are carefully monitored by HPLC, and only the fractions showing substantial purity are pooled.

Specific optical rotation of the isolated and purified Ucn peptide is measured on a Perkin Elmer Model 241 Polarimeter as $[\alpha]_D = -62.50 \pm 1.0$ (c=1 in 1% acetic acid, without correction for the presence of $H_2O$ and TFA); it has a purity of greater than about 95%. Purity is further confirmed by mass spectroscopy and capillary zone electrophoresis (CZE). Liquid secondary ion mass spectrometry (LSIMS) mass spectra are measured with a JEOL model JMS-HX110 double-focusing mass spectrometer fitted with a $Cs^+$ gun. An accelerating voltage of 10 kV and $Cs^+$ gun voltage between 25 and 30 kV are employed. The measured value of 4705.36 Da obtained using LSIMS is in agreement with the calculated value of 4705.52 Da.

To verify the precise sequence, the Ucn peptide is hydrolyzed in sealed evacuated tubes containing constant boiling HCl, 3 $\mu$l of thioglycol/ml. and 1 nmol of Nle (as an internal standard) for 9 hours at 140° C. Amino acid analyses of the hydrolysates using a standard amino acid analyzer shows the expected amino acid ratios, which confirms that a 40-residue peptide structure is obtained with the expected amino acid residues which constitute the intended sequence.

To provide a labelled Ucn peptide for use in assays, including binding assays and the like, the synthesis is extended to link Tyr to Asp at the N-terminus, producing the 41-residue peptide referred to as [Tyr°]-Ucn, which can be readily iodinated with $^{125}I$ and then used in diagnostic assays and in drug-screening assays.

To test the ability of purified Ucn or another candidate Ucn-like peptide to function as a CRF agonist and to promote ACTH production and/or secretion, cultures of dispersed primary murine anterior pituitary cells (0.15×10$^6$ cells/well are used), as generally described in Vale et al. Meth. Enzym., 103, 565–577 (1983), and in Endocrinology, 91, 562 (1972). These cultures are maintained in 0.5 ml/well of β-PJ (a reagent available from Kansas City Biochemicals) containing 2% fetal bovine serum. On the morning of culture day 5, the cells are washed 3 times with β-PJ containing 0.1% bovine serum albumin and then incubated for 1 hour at 37° C. in the same medium. The medium is then replaced with Ucn, or an analog thereof, diluted in β-PJ containing 0.1% bovine serum albumin. Incubations are terminated after 3 hours, at which time the medium is removed and stored at −20° C. until ACTH radioimmunoassays are performed using a suitable kit, such as that commercially available from Diagnostic Products Corporation of Los Angeles, Calif. Secreted ACTH is measured using Allfit computer program with results expressed as the average ±s.e.m. of 3 replicate bioassays.

The rUcn peptide strongly stimulates the secretion of ACTH and β-endorphin in cultured rodent pituitary cells. It is more biopotent than either r/hCRF or sauvagine, having an $EC_{50}$ of about 0.006±0.003 nanomolar, compared to about 0.043±0.012 nM and about 0.033±0.010 nM, respectively; it is also more potent than oCRF. In addition, it is more potent than suckerfishUI (sfUI) which has an $EC_{50}$ of 0.017±0.003. rUcn also stimulates ACTH and β-END-LI secretion in vivo in rats to a greater extent than r/hCRF; in fact, at 30 minutes, a 1 $\mu$g/kg dose of rUcn elevates ACTH level in plasma to a substantially greater extent (659±53 pg/ml) than does a 5 $\mu$g/kg dose of r/hCRF (422±66 pg/ml), using an assay as generally described in Science, 218, 377 (1982). Such a greater effect continues at 1 hour and at 2 hours. The peptide when administered peripherally, e.g. iv, also causes a marked fall in mean arterial blood pressure in rats at a dose as low as 250 ng for a standard laboratory rat of about 250 to 275 grams. At a dose of about 3.77 $\mu$g/kg, it lowers blood pressure 2–3 times as much as either sfUI or r/hCRF and for a longer duration.

Testing is also carried out for the ability of Ucn to cause elevation of the level of intracellular cAMP in cells which express murine CRF-R1 and also in cells which express murine CRF-R2β using an assay as generally described in Chen et al., Expression Cloning of a Human Coritcotropin Releasing Factor (CRF) Receptor, P.N.A.S., 90, 8967–8971 (1993). rUcn is slightly more potent than either r/hCRF or sfUI in elevating cAMP levels in cells expressing mCRF-R1. However, the effect is even more dramatic in assays utilizing cells expressing mCRF-R2β wherein the $ED_{50}$ for rUcn is 0.18±0.04 nanomolar, compared to an $ED_{50}$ for r/hCRF of 1.7±0.4 nM and an $ED_{50}$ for urotensin of 0.74±0.1 nM. It is also more potent than sauvagine which exhibits an $ED_{50}$ of 0.5±0.2.

Binding assays with cells expressing human CRF-R1 are carried out as described in the Chen et al. P.N.A.S., supra. The affinities of test peptides for CRF-R1 and CRF-R2β stably expressed in CHO cells were determined by competitive displacement of $^{125}I$-(Nle$^{21}$, Tyr$^{32}$) ovine CRF (for CRF-R1) or of [$^{125}I$-Tyr°-]Ucn (for CRF-R2β) as described. Data from at lest 3 experiments were pooled and inhibitory dissociation constant ($K_i$) values (95% confidence limits) were calculated using the LIGAND program of Munson and Rodbard (1980), Anal. Biochem, 107:220–239. The cloned hCRF-R1 binds Ucn with high affinity as determined by the competitive displacement of bound radioligand. The $K_i$ for rUcn was determined to be about 0.16(0.08–0.32)nM, compared to r/hCRF of about 0.95(0.47–2.0)nM, sfUI of about 0.43(0.23–0.81)nM, and sauvagine of about 1.2(0.54–2.5) nM. Again, the difference is even more dramatic for similar stably transfected CHO cells expressing human CRF-R2β where the respective results were 0.41(0.26–0.66)nM, 17(10–29)nM, 3.0(1.8–4.8)nM and 2.0(1.1–3.6)nM. Testing also shows that rUcn binds more strongly than does r/hCRF to human CRF binding protein (hCRF-BP) by a factor of about 2, using a competitive hCRF-BP ligand binding assay with the radioligand $^{125}I$[Nle$^{21}$, Tyr$^{32}$]-oCRF, much more strongly than does sauvagine, but less strongly than sfUI.

EXAMPLE IA

Human Ucn(1–40) having the formula (see SEQ ID NO:15):
H-Asp-Asn-Pro-Ser-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ is synthesized in the manner described in Example I. LSIMS shows a value of 4694.31 Da which agrees with the calculated value of 4694.51 Da. In vitro testing for ACTH secretion using anterior pituitary cell cultures as set forth in Example I shows that the peptide is about 3 times as effective as r/hCRF, i.e. 3.10 (1.41–6.65). The peptide also has significant mammalian vasodilatory-hypotensive activity, including lowering systemic blood pressure and stimulating the secretion of ACTH.

EXAMPLE IB

The peptide [Tyr°]rUcn(1–40) having the amino acid sequence (see SEQ ID NO:17):
H-Tyr-Asp-Asp-Pro-Pro-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile- Phe-Asp-Ser-Val-NH$_2$ is synthesized in the manner described in Example I. LSIMS shows a value of 4868.58 Da which agrees perfectly with the calculated value of 4868.58 Da. In vitro testing for ACTH secretion using anterior pituitary cell cultures as set forth in Example I shows that the peptide is about twice as effective as r/hCRF, i.e. 2.20 (1.28–3.88). The peptide also has significant mammalian vasodilatory-hypotensive activity, including lowering systemic blood pressure and stimulating the secretion of ACTH.

EXAMPLE IC

The peptide [D-Tyr$^o$]hUcn(1–40) having the formula:
H-D-Tyr-Asp-Asn-Pro-Ser-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ is synthesized in the manner described in Example I. LSIMS shows a value of 4857.37 Da which agrees with the calculated value of 4857.58 Da. In vitro testing for ACTH secretion using anterior pituitary cell cultures as set forth in Example I shows that the peptide is about 1.25 times as effective as r/hCRF, i.e. 1.23 (0.60–2.54). The peptide also has significant mammalian vasodilatory-hypotensive activity, including lowering systemic blood pressure and stimulating the secretion of ACTH.

EXAMPLE II

The peptide [Ac-Pro$^3$]-hUcn(3–40) having the amino acid sequence (see SEQ ID NO:15):
Ac-Pro-Ser-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ is synthesized in the manner described in Example I but, in addition, the N-terminus is subjected to acetylation by treatment with acetic anhydride after removal of the BOC-protecting group. The resultant peptide likewise stimulates the secretion of ACTH and β-END-LI and causes vasodilatory-hypotensive activity, including lowering of systemic blood pressure.

EXAMPLE IIA

The peptide (cyclo 29–32) [Ac-Pro$^3$,D-Phe$^{11}$, Glu$^{29}$, D-Glu$^{31}$, Lys$^{32}$]-hUcn(3–40) having the amino acid sequence:
Ac-Pro-Ser-Leu-Ser-Ile-Asp-Leu-Thr-D-Phe-His-Leu-Leu-Arg-Thr-Leu-Leu-Glu-Leu-Ala-Arg-Thr-Gln-Ser-Gln-Arg-Glu-Glu-Ala-D-Glu-Lys-Asn-Arg-Ile-Ile-Phe-Asp-Ser-Val-NH$_2$ is synthesized in the manner as generally described in Example I but, in addition, the N-terminus is subjected to acetylation by treatment with acetic anhydride after removal of the BOC-protecting group. The cyclizing lactam bond is created as described in Example I of U.S. Pat. No. 5,064,939. LSIMS shows a value of 4562.36 Da which agrees with the calculated value of 4462.42 Da. In vitro testing for ACTH secretion using anterior pituitary cell cultures as set forth in Example I shows that the peptide is about 6 times as effective as r/hCRF, i.e. 6.14 (2.83–14.05). The resultant peptide likewise stimulates the secretion of ACTH and β-END-LI and causes vasodilatory-hypotensive activity, including lowering of systemic blood pressure.

EXAMPLE IIB

The peptide (cyclo 29–32) [Ac-Pro$^3$,D-Pro$^4$,D-Phe$^{11}$, Glu$^{29}$, Lys$^{32}$]-hUcn(3–40) having the amino acid sequence:
Ac-Pro-D-Pro-Leu-Ser-Ile-Asp-Leu-Thr-D-Phe-His-Leu-Leu-Arg-Thr-Leu-Leu-Glu-Leu-Ala-Arg-Thr-Gln-Ser-Gln-Arg-Glu-Glu-Ala-Glu-Lys-Asn-Arg-Ile-Ile-Phe-Asp-Ser-Val-NH$_2$ is synthesized in the manner as generally described in Example I but, in addition, the N-terminus is subjected to acetylation by treatment with acetic anhydride after removal of the BOC-protecting group. The cyclizing lactam bond is created as described in Example I of U.S. Pat. No. 5,064,939. LSIMS shows a value of 4472.40 Da which agrees with the calculated value of 4472.44 Da. In vitro testing for ACTH secretion using anterior pituitary cell cultures as set forth in Example I shows that the peptide is about 10 times as effective as r/hCRF, i.e. 9.90 (4.48–22.85). The resultant peptide likewise stimulates the secretion of ACTH and β-END-LI and causes vasodilatory-hypotensive activity, including lowering of systemic blood pressure.

EXAMPLE IIC

The peptide (cyclo 29–32) [Ac-Pro$^3$,D-Ser$^4$,D-Phe$^{11}$, Glu$^{29}$, Lys$^{32}$]-hUcn(3–40) having the amino acid sequence:
Ac-Pro-D-Ser-Leu-Ser-Ile-Asp-Leu-Thr-D-Phe-His-Leu-Leu-Arg-Thr-Leu-Leu-Glu-Leu-Ala-Arg-Thr-Gln-Ser-Gln-Arg-Glu-Glu-Ala-Glu-Lys-Asn-Arg-Ile-Ile-Phe-Asp-Ser-Val-NH$_2$ is synthesized in the manner as generally described in Example I but, in addition, the N-terminus is subjected to acetylation by treatment with acetic anhydride after removal of the BOC-protecting group. The cyclizing lactam bond is created as described in Example I of U.S. Pat. No. 5,064,939. LSIMS shows a value of 4462.33 Da which agrees with the calculated value of 4462.42. In vitro testing for ACTH secretion using anterior pituitary cell cultures as set forth in Example I shows that the peptide is about 5.75 times as effective as r/hCRF, i.e. 5.69 (2.43–14.49). The resultant peptide likewise stimulates the secretion of ACTH and β-END-LI and causes vasodilatory-hypotensive activity, including lowering of systemic blood pressure.

EXAMPLE III

The peptide hUcn(2–40) having the amino acid sequence (see SEQ ID NO:15):
H-Asn-Pro-Ser-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ is synthesized in the manner described in Example I. The peptide has significant mammalian vasodilatory-hypotensive activity, including lowering systemic blood pressure and stimulating the secretion of ACTH.

EXAMPLE IV

The peptide [D-Phe$^{11}$]-hUcn having the amino acid sequence: H-Asp-Asn-Pro-Ser-Leu-Ser-Ile-Asp-Leu-Thr-D-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ is synthesized in the manner described in Example I. The peptide has significant mammalian vasodilatory-hypotensive activity, including lowering systemic blood pressure and stimulating the secretion of ACTH.

EXAMPLE V

The peptide agonist analogs of hUcn as set forth hereinafter, which are considered to have substantially the same amino acid sequence as hUcn, are synthesized:

| | |
|---|---|
| [Glu¹]-hUcn | [Leu³⁶]-hUcn |
| [Ile⁵]-hUcn | [Ile¹⁸]-hUcn |
| [Val¹⁷]-hUcn | [Ile²⁰]-hUcn |
| [Lys²²]-hUcn | [Lys²⁷]-hUcn |
| [Leu³⁵]-hUcn | [Leu³⁷]-rUcn |
| [Glu³⁸]-hUcn | [Ile⁴⁰]-rUcn |
| [Ser¹⁰]-hUcn | [Thr³⁹]-rUcn |
| [Leu¹¹]-hUcn | [Leu⁷]-rUcn |
| [Glu²]-hUcn | [Leu⁷,¹¹]-rUcn |
| [Gln²⁹]-hUcn | [Lys²²,²⁷]-rUcn |
| [Asn³²]-hUcn | [Ile⁵, Gln²⁹]-rUcn |

Each of the foregoing Ucn-like agonist peptides has significant mammalian vasodilatory-hypotensive activity, including lowering systemic blood pressure and stimulating the secretion of ACTH.

EXAMPLE VI

A further group of Ucn-like agonist peptides are synthesized which fall within the following amino acid sequence:
Y-Asp-Asn-Pro-Ser-Leu-Ser-Ile-Asp-Leu-Thr-D-Phe-His-Leu-Leu-Arg-Thr-Leu-Leu-R₁₉-Leu-Ala-Arg-Thr-Gln-Ser-Gln-Arg-Glu-R²⁹-Ala-Glu-R₃₂-Asn-Arg-Ile-R₃₆-Phe-R₃₈-Ser-Val-NH₂, wherein Y is an acyl group having 7 or less carbon atoms or hydrogen; R₁₉ is Glu or Ala; R₂₉ is Arg, Glu, Lys or Orn; R₃₂ is Gln, Lys, Orn or Glu; R₃₆ is Ile, CᵅMeIle or CᵅMeLeu; R₃₈ is Asp or Ala; provided that when R₂₉ is Glu, R₃₂ is either Lys or Orn and the side chains thereof are linked by an amide bond, and that when R₂₉ is either Lys or Orn, R₃₂ is Glu, and the side chains thereof are linked by an amide bond. In this group, D-Phe¹¹ can be replaced by D-Leu or by a D-isomer of another natural α-amino acid; Glu in the 31-position can be replaced by a D-isomer, e.g. D-Glu, D-Arg, imBzlD-His, etc.; and the N-terminus can be shortened by 1 or 2 residues.

The specific peptides are as follows:
[Ac-Pro³,D-Phe¹¹]-hUcn(3–40)
[D-Leu¹¹, Ala¹⁹]-hUcn
[D-Phe¹¹, Ala³⁸]-hUcn
[D-Tyr¹¹, CᵅMeIle³⁶]-hUcn
[D-Phe¹¹, CᵅMeLeu³⁶]-hUcn
[Ac-Asp¹, D-Phe¹¹, Ala¹⁹,³⁸]-hUcn
(cyclo 29–32)[D-Leu¹¹, Glu²⁹, Lys³²]-hUcn
(cyclo 29–32)[D-Phe¹¹, Glu²⁹, Orn³²-]hUcn(2–40)
(cyclo 29–32)[Ac-Pro³,D-Phe¹¹, Lys²⁹, Glu³²]-hUcn (3–40)
(cyclo 29–32)[D-Tyr¹¹, Orn²⁹, Glu³²]-hUcn(3–40)
(cyclo 29–32)[D-Phe¹¹, Glu²⁹, D-Glu³¹, Lys³²]-hUcn
(cyclo 29–32)[D-Phe¹¹, Glu²⁹, D-Arg³¹, Lys³²]-hUcn
(cyclo 29–32)[D-Tyr¹¹, Glu²⁹, imBzD-His³¹, Lys³²]-hUcn Each of the foregoing Ucn-like agonist peptides has significant mammalian vasodilatory-hypotensive activity, including lowering systemic blood pressure and stimulating the secretion of ACTH.

EXAMPLE VII

A still further group of Ucn-like agonist peptides are synthesized which fall within the following amino acid sequence (SEQ ID NO: 14):
Y-Xaa₁-Xaa₂-Pro-Xaa₄-Xaa₅-Ser-Xaa₇-Asp-Leu-Xaa₁₀-Xaa₁₁-Xaa₁₂-Xaa₁₃-Leu-Arg-Xaa₁₆-Xaa₁₇-Xaa₁₈-Xaa₁₉-Xaa₂₀-Xaa₂₁-Xaa₂₂-Xaa₂₃-Xaa₂₄-Xaa₂₅-Xaa₂₆-Xaa₂₇-Xaa₂₈-Xaa₂₉-Ala-Xaa₃₁-Xaa₃₂-Asn-Arg-Xaa₃₅-Xaa₃₆-Xaa₃₇-Xaa₃₈-Xaa₃₉-Xaa₄₀-NH₂, wherein Y is an acyl group having 7 or less carbon atoms or hydrogen; Xaa₁ is Asp, Glu or Gln; Xaa₂ is Asn, Asp, Glu or Gly; Xaa₄ is Ser or Pro; Xaa₅ is Leu, Ile or Met; Xaa₇ is Ile or Leu; Xaa₁₀ is Thr or Ser; Xaa₁₁ is Phe or Leu; Xaa₁₂ is His or Glu; Xaa₁₃ is Leu or Met; Xaa₁₆ is Thr, Asn, Glu, or Lys; Xaa₁₇ is Leu, Met or Val; Xaa₁₈ is Leu or Ile; Xaa₁₉ is Glu or His; Xaa₂₀ is Leu, Met, Ile or Arg; Xaa₂₁ is Ala, Glu or Thr; Xaa₂₂ is Arg or Lys; Xaa₂₃ is any natural amino acid and preferably Thr, Ser, Ala, Ile, Met, Val, Asn, Gln, Gly, Lys, His, Leu, Glu or Asp; Xaa₂₄ is Gln, Glu or Asp; Xaa₂₅ is any natural amino acid and preferably Ser, Thr, Ala, Ile, Met, Val, Asn, Gln, Gly, Lys, His, Leu, Glu or Asp; Xaa₂₆ is Gln, Leu or Glu; Xaa₂₇ is Arg, Ala or Lys; Xaa₂₈ is Glu or Gln; Xaa₂₉ is Arg or Gln; Xaa₃₁ is any natural amino acid and preferably Ala, Ile, Met, Val, Asn, Gln, Gly, Lys, His, Leu, Glu or Asp; Xaa₃₂ is any natural amino acid and preferably Ala, Ile, Met, Val, Asn, Gln, Gly, Lys, His, Leu, Glu or Asp; Xaa₃₅ is Ile, Lys, Leu or Asn; Xaa₃₆ is Ile, Tyr, Met or Leu; Xaa₃₇ is Phe, Leu or Met; Xaa₃₈ is Asp or Glu; Xaa₃₉ is Ser, Ile, Glu or Thr; and Xaa₄₀ is Val, Ile, Phe or Ala; provided that there are no more than 3 residues different from Ucn, and that the N-terminus may be shortened by 1 or 2 residues.

The following specific peptides are synthesized:

| | |
|---|---|
| [Ac-Pro³,Met⁵]-hUcn(3-40) | |
| [Glu¹²]-hUcn | [Met¹³]-hUcn |
| [Asn¹⁶, Ala³²]-hUcn | [Glu¹⁶, Ala²⁵,³¹]-hUcn |
| [Lys¹⁶, Ile²³, Ala³²]-hUcn | [Val¹⁷, Ile²⁵, Met³¹]-hUcn |
| [Met¹⁷, Ile³¹,³²]-hUcn | [Ser¹⁰, Ile¹⁸, His¹⁹]-hUcn |
| [Glu¹, Met²⁰, Lys³⁵]-hUcn | [Ile²⁰, Met³², Glu³⁸]-hUcn |
| [Arg²⁰, Asn²³, Thr²⁵]-hUcn | [Thr²¹, Gly²³,³²]-hUcn |
| [Glu²¹, Lys²³, Gln²⁸]-hUcn | [Lys²², His²³, Leu³¹]-hUcn |
| [Val²³, Glu²⁴, Met³⁶]-hUcn | [Gln²³, Asp²⁵, Glu³⁹]-hUcn |
| [Met²³, Gly²⁵, Leu³⁵]-hUcn | [Glu²³, Tyr³⁶, Phe⁴⁰]-hUcn |
| [Asp²³, Lys²⁷, Leu³²]-hUcn | [Ser²³, Asp²⁴, Met²⁵]-hUcn |
| [Ac-Pro³,Leu²³,²⁵, Gln²⁹]-hUcn(3-40) | |
| [Asn²⁵,³², Ile³⁹]-hUcn | [Gln²⁵,³¹, Asn³⁵]-hUcn |
| [Lys²⁵, Val³¹, Ala³²]-hUcn | [Glu², Asn³¹, His³²]-hUcn |
| [Gln¹, Ile⁵, Val³²]-hUcn | [Gly², Leu¹¹, Thr³¹]-hUcn |
| [Glu²⁵, Leu³⁷]-hUcn | [Ile⁵, His²⁵, Ala⁴⁰]-hUcn |
| [Leu⁷, His³¹, Asp³²]-hUcn | [Gln³², Leu³⁶, Ala⁴⁰]-hUcn |
| [His²⁵, Ala³¹, Thr³⁹]-hUcn | [Leu²⁶, Lys³¹, Thr²³]-hUcn |
| [Glu²⁶, Ala²⁷, Lys³²]-hUcn | [Lys²⁷, Asp³¹, Met³⁷]-hUcn |
| [Ac-Pro³,Val²⁵, Leu³⁶]-hUcn(3-40) | |
| [Ala²⁵, Asp³¹, Ile⁴⁰]-hUcn | [Val³², Leu³⁷, Ile³⁹]-hUcn |
| [Leu¹¹, Ile¹⁸, Thr³⁹]-hUcn | |

Each of the foregoing Ucn-like agonist peptides has significant mammalian vasodilatory-hypotensive activity, including lowering systemic blood pressure and stimulating the production of ACTH.

The following group of Examples are directed to N-terminally shortened versions (e.g. shortened by 7–10 residues) of the Ucn-like peptides which have antagonistic properties. All of the statements made hereinbefore with respect to the chemical character and/or the synthesis of Ucn analogs are considered to apply equally to the antagonists and are not thus repeated; the antagonists are merely N-terminally shortened versions of the agonists. The specific peptides set forth in the following Examples exhibit antagonistic biological properties with respect to the effect of Ucn on at least the CRF receptors, CRF-R1, and CRF-R2. In this respect these Ucn-antagonists are considered to generally at least have characteristics and uses similar to those described for CRF antagonists in U.S. Pat. No. 5,245,009.

EXAMPLE VIII

The peptide, Ucn(11–40), having the amino acid sequence (see SEQ ID NO:8):
H-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ is synthesized in the manner described in Example I. To evaluate the biological activity of a candidate peptide as a Ucn antagonist (which will be indicative of its effective binding to CRF receptors), the previously mentioned assay from *Endocrinology*, 91, supra, is run in the presence of a challenge dose of ovine CRF. The performance of such candidate in this assay is routinely compared to the performance of a highly potent linear CRF antagonist, i.e. [D-Phe$^{12}$, Nle$^{21,38}$]-r/hCRF(12–41) which is hereinafter referred to as the Standard Antagonist. An in vivo test measuring elevation of mean arterial blood pressure as a result of iv injection is also simply and straightforwardly performed. The peptide Ucn(11–40) exhibits significant mammalian vasoconstrictive activity causing elevation of mean arterial blood pressure, as do known CRF antagonists.

The synthesis is repeated twice to produce Ucn (10–40) and [Ac-Thr$^{10}$]Ucn(10–40); both show bioactivity as Ucn antagonists.

EXAMPLE IX

The peptide, [D-Phe$^{11}$]-Ucn(11–40), having the amino acid sequence:
H-D-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ is synthesized in the manner described in Example I. Its specific optical rotation is measured under the conditions set forth hereinbefore as [α]$_D$=−62°±1.0. LSIMS shows a value of 3638.88 Da which agrees with the calculated value of 3639.00 Da. In vitro testing is carried out as described in Example VIII, which demonstrates the peptide is bioactive, exhibiting a value of 0.551 (0.333–0.857) compared to this highly biopotent Standard Antagonist. The peptide has significant mammalian vasoconstrictive activity, causing elevation of mean arterial blood pressure, indicative of its being a Ucn antagonist.

EXAMPLE X

The peptide, [D-Tyr$^{11}$]-Ucn(11–40), having the amino acid sequence:
H-D-Tyr-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ is synthesized in the manner described in Example I. The peptide has significant mammalian vasoconstrictive activity causing elevation of mean arterial blood pressure, indicative of its being a Ucn antagonist. It is also effectively iodinated to provide [$^{125}$I-D-Tyr$^{11}$]-Ucn(11–40) for use in screening assays and the like.

EXAMPLE XI

The peptide, (cyclo 29–32)[D-Phe$^{11}$, Glu$^{29}$, Lys$^{32}$]-Ucn (11–40), having the amino acid sequence:
H-D-Phe-His-Leu-Leu-Arg-Thr-Leu-Leu-Glu-Leu-Ala-Arg-Thr-Gln-Ser-Gln-Arg-Glu-Glu-Ala-Glu-Lys-Asn-Arg-Ile-Ile-Phe-Asp-Ser-Val-NH$_2$ is synthesized in the manner described in Example I, with the cyclizing lactam bond being created as described in Example I of U.S. Pat. No. 5,064,939, issued Nov. 12, 1991. Its specific optical rotation is measured under the conditions set forth hereinbefore as [α]$_D$=−49°±1.0. LSIMS shows a value of 3593.89 Da which agrees with the calculated value of 3593.97 Da. In vitro testing for ACTH secretion using anterior pituitary cell cultures as set forth in Example VIII shows that the peptide is about 10 times as effective as the Standard Antagonist, i.e. 10.34 (4.27–25.58). The peptide also has significant mammalian vasoconstrictive activity causing elevation of mean arterial blood pressure, indicative of its being a Ucn antagonist.

EXAMPLE XII

The peptide, (cyclo 29–32)[D-Tyr$^{11}$, Glu$^{29}$, Lys$^{32}$]-Ucn (11–40), having the amino acid sequence:
H-D-Tyr-His-Leu-Leu-Arg-Thr-Leu-Leu-Glu-Leu-Ala-Arg-Thr-Gln-Ser-Gln-Arg-Glu-Glu-Ala-Glu-Lys-Asn-Arg-Ile-Ile-Phe-Asp-Ser-Val-NH$_2$ is synthesized in the manner described in Example I, with the cyclizing lactam bond being created as described in Example I of U.S. Pat. No. 5,064,939. LSIMS shows a value of 3609.82 Da which agrees with the calculated value of 3609.96 Da. In vitro testing for ACTH secretion using anterior pituitary cell cultures as set forth in Example VIII shows that the peptide is about 4 times as effective as the Standard Antagonist, i.e. 4.01 (2.32–7.05). The peptide has significant mammalian vasoconstrictive activity causing elevation of mean arterial blood pressure, indicative of its being a Ucn antagonist. It is also iodinated to provide $^{125}$I-D-Tyr$^{11}$ cyclic analog for use in screening assays and the like.

EXAMPLE XIIA

The peptide, (cyclo 29–32)[D-Tyr$^{11}$, Glu$^{29}$, D-Glu$^{31}$, Lys$^{32}$]-Ucn(11–40), having the amino acid sequence:
H-D-Tyr-His-Leu-Leu-Arg-Thr-Leu-Leu-Glu-Leu-Ala-Arg-Thr-Gln-Ser-Gln-Arg-Glu-Glu-Ala-D-Glu-Lys-Asn-Arg-Ile-Ile-Phe-Asp-Ser-Val-NH$_2$ is synthesized in the manner described in Example I, with the cyclizing lactam bond being created as described in Example I of U.S. Pat. No. 5,064,939. The peptide has significant mammalian vasoconstrictive activity causing elevation of mean arterial blood pressure, indicative of its being a Ucn antagonist. It is also iodinated to provide $^{125}$I-D-Tyr$^{11}$ cyclic analog for use in screening assays and the like.

EXAMPLE XIII

The peptide, (cyclo 29–32)[D-Phe$^{11}$, Glu$^{29}$, D-Glu$^{31}$, Lys$^{32}$]-Ucn(11–40), having the amino acid sequence:
H-D-Phe-His-Leu-Leu-Arg-Thr-Leu-Leu-Glu-Leu-Ala-Arg-Thr-Gln-Ser-Gln-Arg-Glu-Glu-Ala-D-Glu-Lys-Asn-Arg-Ile-Ile-Phe-Asp-Ser-Val-NH$_2$ is synthesized in the manner described in Example I, with the cyclizing lactam bond being created as described in Example I of U.S. Pat. No. 5,064,939. LSIMS shows a value of 3593.80 Da which agrees with the calculated value of 3593.97. In vitro testing for ACTH secretion using anterior pituitary cell cultures as set forth in Example VIII shows that the peptide is about 4.75 times as effective as the Standard Antagonist, i.e. 4.72 (2.19–10.00). The peptide also has significant mammalian vasoconstrictive activity causing elevation of mean arterial blood pressure, indicative of its being a Ucn antagonist.

The synthesis is repeated twice to substitute D-Leu and D-His for D-Phe. The peptides show similar bioactivity as Ucn antagonists.

EXAMPLE XIIIA

The peptide, (cyclo 29–32)[Pro$^{10}$,D-Phe$^{11}$, Glu$^{29}$, D-Glu$^{31}$, Lys$^{32}$]-Ucn(10–40), having the amino acid sequence:

H-Pro-D-Phe-His-Leu-Leu-Arg-Thr-Leu-Leu-Glu-Leu-Ala-Arg-Thr-Gln-Ser-Gln-Arg-Glu-Glu-Ala-D-Glu-Lys-Asn-Arg-Ile-Ile-Phe-Asp-Ser-Val-NH$_2$ is synthesized in the manner described in Example I, with the cyclizing lactam bond being created as described in Example I of U.S. Pat. No. 5,064,939. LSIMS shows a value of 3690.91 Da which agrees with the calculated value of 3691.02 Da. In vitro testing for ACTH secretion using anterior pituitary cell cultures as set forth in Example VIII shows that the peptide is about 2.75 times as effective as the Standard Antagonist, i.e. 2.74 (1.02–8.02). The peptide also has significant mammalian vasoconstrictive activity causing elevation of mean arterial blood pressure, indicative of its being a Ucn antagonist. This synthesis and testing show that the inclusion of an additional L-isomer at the N-terminus does not significantly alter its bioactivity as a Ucn antagonist.

EXAMPLE XIIIB

The peptide, (cyclo 29–32)[D-Pro$^{10}$,D-Phe$^{11}$, Glu$^{29}$, D-Glu$^{31}$, Lys$^{32}$]-Ucn(10–40), having the amino acid sequence:

H-D-Pro-D-Phe-His-Leu-Leu-Arg-Thr-Leu-Leu-Glu-Leu-Ala-Arg-Thr-Gln-Ser-Gln-Arg-Glu-Glu-Ala-D-Glu-Lys-Asn-Arg-Ile-Ile-Phe-Asp-Ser-Val-NH$_2$ is synthesized in the manner described in Example I, with the cyclizing lactam bond being created as described in Example I of U.S. Pat. No. 5,064,939. LSIMS shows a value of 3691.00 Da which agrees with the calculated value of 3691.02 Da. In vitro testing for ACTH secretion using anterior pituitary cell cultures as set forth in Example VIII shows that the peptide is about 5 times as effective as the Standard Antagonist, i.e. 4.99 (2.26–11.55). The peptide also has significant mammalian vasoconstrictive activity causing elevation of mean arterial blood pressure, indicative of its being a Ucn antagonist. This synthesis and testing show that the inclusion of an additional D-isomer at the N-terminus does not significantly alter the bioactivity of a Ucn antagonist, as by comparison to Peptide XIII.

EXAMPLE XIV

The peptide, (cyclo 29–32)[D-Phe$^{11}$, Glu$^{29}$, D-Arg$^{31}$, Orn$^{32}$]-Ucn(11–40), having the amino acid sequence:

H-D-Phe-His-Leu-Leu-Arg-Thr-Leu-Leu-Glu-Leu-Ala-Arg-Thr-Gln-Ser-Gln-Arg-Glu-Glu-Ala-D-Arg-Orn-Asn-Arg-Ile-Ile-Phe-Asp-Ser-Val-NH$_2$ is synthesized in the manner described in Example I, with the cyclizing lactam bond being created as described in Example I of U.S. Pat. No. 5,064,939. The peptide has significant mammalian vasoconstrictive activity causing elevation of mean arterial blood pressure, indicative of its being a Ucn antagonist.

The synthesis is repeated twice substituting imBzlD-His and D-2Nal for D-Arg and twice again to also add Ac-Thr at the N-terminus with these substitutions. All four peptides show good bioactivity as Ucn antagonists.

EXAMPLE XV

The peptide, (cyclo 29–32)[D-Phe$^{11}$, Lys$^{29}$, Glu$^{32}$]-Ucn (11–40), having the amino acid sequence:

H-D-Phe-His-Leu-Leu-Arg-Thr-Leu-Leu-Glu-Leu-Ala-Arg-Thr-Gln-Ser-Gln-Arg-Glu-Lys-Ala-Glu-Glu-Asn-Arg-Ile-Ile-Phe-Asp-Ser-Val-NH$_2$ is synthesized in the manner described in Example I, with the cyclizing lactam bond being created as described in Example I of U.S. Pat. No. 5,064,939. The peptide has significant mammalian vasoconstrictive activity causing elevation of mean arterial blood pressure, indicative of its being a Ucn antagonist.

EXAMPLE XVI

The peptide, (cyclo 29–32)[D-Phe$^{11}$, Lys$^{29}$, D-Glu$^{31}$, Glu$^{32}$]-Ucn(11–40), having the amino acid sequence:

H-D-Phe-His-Leu-Leu-Arg-Thr-Leu-Leu-Glu-Leu-Ala-Arg-Thr-Gln-Ser-Gln-Arg-Glu-Lys-Ala-D-Glu-Glu-Asn-Arg-Ile-Ile-Phe-Asp-Ser-Val-NH$_2$ is synthesized in the manner described in Example I, with the cyclizing lactam bond being created as described in Example I of U.S. Pat. No. 5,064,939. The peptide has significant mammalian vasoconstrictive activity causing elevation of mean arterial blood pressure, indicative of its being a Ucn antagonist.

EXAMPLE XVII

Additional Ucn antagonist peptides, as set forth as follows, many of which are considered to be substantially the same as Ucn(11–40), are synthesized in the manner described in Example I:

| | |
|---|---|
| [Val$^{17}$]-rUcn(11-40) | [C$^\alpha$MeLeu$^{36}$]-rUcn(11-40) |
| [Lys$^{22}$]-rUcn(8-40) | [D-Phe$^{11}$, Ile$^{18}$]-rUcn(11-40) |
| [Ac-Asp$^8$,Lys$^{22}$]-Ucn(8-40) | [Leu$^{35}$]-rUcn(11-40) |
| [Ile$^{20}$]-rUcn(10-40) | [Ac-Thr$^{10}$,Ile$^{20}$]-Ucn(10-40) |
| [Glu$^{38}$]-rUcn(11-40) | [D-Phe$^{11}$, Lys$^{27}$]-rUcn(11-40) |
| [Ser$^{10}$]-rUcn(10-40) | [C$^\alpha$MeIle$^{36}$, Leu$^{37}$]-rUcn(11-40) |
| [D-Leu$^{11}$]-rUcn(11-40) | [Ala$^{38}$,Ile$^{40}$]-rUcn(11-40) |
| [Gln$^{29}$]-rUcn(9-40) | [Ala$^{19}$, Thr$^{39}$]-rUcn(11-40) |
| [Asn$^{32}$]-rUcn(11-40) | [D-Phe$^{11}$, Lys$^{22,27}$]-rUcn(11-40) |
| [Ac-Leu$^9$,Gln$^{29}$]-Ucn(9-40) | [Lys$^{22}$, Gln$^{29}$]-rUcn(11-40) |

Each of the foregoing Ucn-like antagonist peptides has significant mammalian vasoconstrictive activity causing elevation of mean arterial blood pressure, indicative of its being a Ucn antagonist.

The following group of Examples are directed to the synthesis of CRF-BP blockers which increase the available amount of endogenous CRF and Ucn by complexing with CRF-BP.

EXAMPLE XVIII

A peptide, Ucn(5–32), having the amino acid sequence (see SEQ ID NO:8):

Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln is synthesized in the manner described in Example I.

A prospective peptide blocker is evaluated using a competitive hCRF-BP ligand binding assay. Binding of [$^{125}$I-DTyr$^0$]hCRF to soluble hCRF-BP is performed in phosphate-buffered saline (PBS) containing 25 mM EDTA, 0.25% bovine serum albumin, and 0.01% Triton X-100, using medium enriched by recombinant CHO cells as a source of hCRF-BP. Reactions are performed in a total volume of 400 µl including 50,000 CPM[$^{125}$I-DTyr$^0$]hCRF. A constant amount of radioactive hCRF and hCRF-BP and varying amounts of the sample peptide are used to carry out competitive binding assays. After an overnight incubation at room temperature, precipitation is accomplished using rabbit anti-hCRF-BP antiserum (1:9000 final dilution) and 200 μl of sheep anti-rabbit IgG solution. After incubating with the primary and secondary antisera for 30 minutes each, 1 ml of saline wash is added, and the test tubes are centrifuged at 2000×g for 20 minutes at 4° C. Precipitates are counted in a gamma counter. Inhibitory binding affinity constant ($K_i$) values are determined using parameters calculated by the LIGAND computer program, Munson et al., *Anal. Biochem.*, 107, 220 (1980), and a Vax/VMS computer system.

The CRF-BP blocker Ucn(5–32) has a $K_i$ lower than that of hCRF(9–33) and thus is a potentially superior blocking agent for increasing the available amount of CRF and/or Ucn.

EXAMPLE XIX

A peptide, Ucn(8–32), having the amino acid sequence (see SEQ ID NO:8):
Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln is synthesized in the manner described in Example I. LDMS shows a value of 3023.48 Da which agrees with the calculated value of 3023.65 Da. Testing shows that the peptide has a $K_i$ lower than that of hCRF(9–33) and thus is a potentially superior blocking agent for increasing the available amount of CRF and/or Ucn.

EXAMPLE XX

A peptide, Ucn(3–27), having the amino acid sequence (see SEQ ID NO:8):
Pro-Pro-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg is synthesized in the manner described in Example I. The peptide has a $K_i$ lower than that of hCRF(9–33) and thus is a potentially superior blocking agent for increasing the available amount of CRF and/or Ucn.

EXAMPLE XXI

A peptide, [Ile$^{18}$]-Ucn(6–29), having the amino acid sequence (see SEQ ID NO:8):
Ser-Ile-Asp-Leu-Thr-Phe-His-Leu-Leu-Arg-Thr-Leu-Ile-Glu-Leu-Ala-Arg-Thr-Gln-Ser-Gln-Arg-Glu-Arg is synthesized in the manner described in Example I. The peptide has a $K_i$ lower than that of hCRF(9–33) and thus is a potentially superior blocking agent for increasing the available amount of CRF and/or Ucn.

Ucn profoundly stimulates the pituitary-adrenalcortical axis and is considered to be useful to stimulate the functions of this axis in some types of patients with low endogenous glucocorticoid production. For example, Ucn and its analogs should be useful in restoring pituitary-adrenal function in patients having received exogenous glucocorticoid therapy whose pituitary-adrenalcortical functions remain suppressed.

Most other regulatory peptides have been found to have effects upon the central nervous system and upon the gastrointestinal tract. Because ACTH and sympathetic nervous system activation secretion is the "sine qua non" of mammal's response to stress, it was not surprising that CRFs have significant effects on the brain as a mediator of the body's stress response. Accordingly, Ucn and its analogs are considered to also find application in modifying the mood, learning, memory and behavior of normal and mentally disordered individuals. Because Ucn elevates the levels of ACTH, β-END, β-lipotropin, other pro-opiomelanocortin gene products and corticosterone, its administration can be used to induce the effects of the foregoing POMC-derived peptides on the brain to thereby influence memory, mood, pain appreciation, etc., and more specifically, alertness, depression and/or anxiety, and also their effects peripherally. For example, when administered directly into the ventricles, CRFs increase physical activity and improve learning performance in rats and thus may function as a natural stimulant; because Ucn similarly activates the CRF receptors, it will function similarly.

Because CRF-R2 has been found to be abundantly expressed in the heart, especially in association with blood vessels, and because it is known that the addition of CRF into the left atrium of an isolated perfused heart induces a prolonged dilatory effect on coronary arteries, transiently produces a positive inotropic effect and stimulates the secretion of atrial natriuretic peptide, it is now believed that Ucn is responsible, at least in part, for regulating cardiac perfusion because of its particularly high affinity for the CRF-R2s. It is also expected that other vascular beds, such as the superior mesenteric, will be dilated by Ucn and its analogs. Because of these biological effects in the heart, Ucn and agonists/antagonists thereof (as well as anti-Ucn antibodies), can be effectively used to selectively modulate cardiac perfusion.

Moreover, because of the localization of CRF-R2 on blood vessels, it is considered that Ucn-like agonist and antagonist peptides of the invention are therapeutically useful to modulate blood flow in many various vascular beds, and particularly in desired tissues and organs. Ucn and its agonist analogs are considered to be of use for increasing blood flow to the gastrointestinal tract of animals, particularly humans and other mammals, because all CRF-related peptides have been shown to dilate the mesenteric vascular bed. CRF and certain fragments have been shown to modulate vascular permeability (Wei E. T. et al., "Peripheral anti-inflammatory actions of corticotropin-releasing factor", pp. 258–276, *Corticotropin-Releasing Factor* (Ciba Foundation Symposium 172) John Wiley & Sons, 1993). Ucn and its fragments will also reduce vascular leakage and have a salutary effect on injury- or surgery-induced tissue swelling and inflammation. Therefore, Ucn and its analogs and fragments that are agonists can be administered parenterally to decrease inflammation, swelling and oedema and to reduce fluid loss following heat injury.

oCRF, r/hCRF, urotensin I and sauvagine have been shown to inhibit gastric acid production, and Ucn and its analogs are considered to also be effective in the treatment of gastric ulcers by reducing gastric acid production and/or inhibiting certain gastrointestinal functions in a mammal. Ucn and its analogs will be effective in increasing intestinal transit rate and useful in the treatment of acute constipation.

A number of direct stimulatory effects of CRF on the GI tract have earlier been described. For example, CRF acts on the gut in vitro to depolarize myenteric neurons in the small intestine. The results of in vivo studies with intravenously administered CRF and CRF antagonists have been consistent with the observed effect of CRF to control gastric emptying and intestinal motility. The Ucn-like peptides of the invention are considered useful in treating intestinal and gastrointestinal disorders, such as irritable bowel syndrome. CRF antagonists have previously been used to therapeutically treat irritable bowel syndrome, and antagonists based upon Ucn (which would be selective for CRF-R2) are considered to be even more useful. These antagonists may also be used to treat spastic colon and Crohn's disease.

These Ucn-like peptides may also be used to evaluate hypothalamic pituitary adrenal function in mammals with suspected endocrine or central nervous system pathology by suitable administration followed by monitoring bodily functions. For example, administration may be used as a diagnostic tool to evaluate Cushing's disease and affective disorders, such as depressive illness.

Ucn, an analog or a nontoxic salt thereof, combined with a pharmaceutically or veterinarily acceptable carrier to form a pharmaceutical composition, may be administered to animals, including humans and other mammals, either intravenously, subcutaneously, intramuscularly, percutaneously, e.g. intranasally, intracerebrospinally or orally. The isolated peptides should be at least about 90% pure and preferably should have a purity of at least about 98%; however, lower purities are effective and may well be used with mammals other than humans. This purity means that the intended peptide constitutes the stated weight % of all like peptides and peptide fragments present. Administration to humans may be employed by a physician to lower blood pressure or to stimulate endogenous gluco-corticoid production. The required dosage will vary with the particular condition being treated, with the severity of the condition and with the duration of desired treatment. Ucn or Ucn analogs can also be administered, e.g., icv, to cause an increase of Ucn in the brain and thereby cause (a) improvement in short to medium term memory in a subject afflicted with Alzheimer's disease; (b) relief from chronic fatigue syndrome; (c) suppression of appetite; (d) stimulation of the respiratory system, (e) improvement in learning performance; (f) improvement in memory; (g) improvement in alertness; (h) reduction of depression and/or (i) lessening of anxiety. Particular effectiveness is shown in appetite suppression.

Such peptides are often administered in the form of pharmaceutically or veterinarily acceptable nontoxic salts, such as acid addition salts or metal complexes, e.g., with zinc, iron, calcium, barium, magnesium, aluminum or the like. Illustrative of such nontoxic salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

It may also be desirable to deliver Ucn or analogs thereof over prolonged periods of time, for example, for periods of one week to one year from a single administration, and slow release, depot or implant dosage forms may be utilized as well known in this art. For example, a dosage form may contain a pharmaceutically acceptable non-toxic salt of the compound which has a low degree of solubility in body fluids, for example, an acid addition salt with a polybasic acid; a salt with a polyvalent metal cation; or combination of the two salts. A relatively insoluble salt may also be formulated in a gel, for example, an aluminum stearate gel. A suitable, slow-release depot formulation for injection may also contain Ucn or an analog or a salt thereof dispersed or encapsulated in a slow degrading, non-toxic or non-antigenic polymer such as a polylactic acid/polyglycolic acid polymer, for example, as described in U.S. Pat. No. 3,773,919.

Therapeutically effective amounts of the peptides should be administered under the guidance of a physician, and pharmaceutical compositions will usually contain the peptide in conjunction with a conventional, pharmaceutically or veterinarily-acceptable carrier. A therapeutically effective amount is considered to be a predetermined amount calculated to achieve the desired effect, e.g. to increase or decrease the amount of ACTH, in a patient. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such compounds in depot or long-lasting form as earlier described. A therapeutically effective amount is typically an amount of a Ucn or an analog thereof that, when administered peripherally in a physiologically acceptable composition, is sufficient to achieve a plasma concentration thereof from about 0.1 $\mu$g/ml to about 100 $\mu$g/ml, preferably from about 1 $\mu$g/ml to about 50 $\mu$g/ml, more preferably at least about 2 $\mu$g/ml and usually 5 to 10 $\mu$g/ml. Antibodies or antisense polynucleotides are also administered in proportionately appropriate amounts in accordance with known practices in this art. The level of ACTH present in a patient, particularly in the plasma, can be readily determined by routine clinical analysis. Changes in ACTH levels can be monitored during a treatment regimen to determine the effectiveness of the administered Ucn-like peptide over time. In some instances, treatment of subjects with these peptides can be carried out in lieu of the administration of ACTH or corticosteroids, in such instances a dosage as low as about 10 ng/Kg of body weight may be employed.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. Although the claims variously define the invention in terms of a peptide sequence, it should be understood that such is intended to include nontoxic salts thereof which are well known to be the full equivalent thereof and which are most frequently administered. Instead of the simple amide at the C-terminus, a lower alkyl-substituted amide, e.g. methylamide, ethylamide, etc, may be incorporated or the C-terminus may be otherwise blocked as well known in the peptide art. Polypeptides having an amino acid residue sequence substantially identical to the sequence of Ucn specifically shown herein, in which one or more residues have been conservatively substituted with a functionally similar residue, are considered to be equivalents of Ucn so long as they mimic a biological function of CRF. Such peptides and salts thereof are considered as being within the scope of the claimed invention.

The disclosures of all patents and publications set forth hereinbefore, as well as of the two priority applications, are expressly incorporated herein by reference. As used herein, all temperatures are °C., and all ratios and percentages of liquid materials are by volume.

SEQUENCE LISTING SUMMARY

SEQ ID NO:1, when the C-terminus is amidated, is the amino acid sequence of ovine CRF.

SEQ ID NO:2, when pGlu is at the N-terminus and the C-terminus is amidated, is the amino acid sequence of frog sauvagine.

SEQ ID NO:3, when the C-terminus is amidated, is the amino acid sequence of rat/human CRF.

SEQ ID NO:4, when the C-terminus is amidated, is the amino acid sequence of suckerfish urotensin.

SEQ ID NO:5, when the C-terminus is amidated, is the amino acid sequence of carp urotensin.

SEQ ID NO:6, when the C-terminus is amidated, is the amino acid sequence of flathead sole (Maggy).

SEQ ID NO:7, when the C-terminus is amidated, is the amino acid sequence of fish CRF.

SEQ ID NO:8, when the C-terminus is amidated, is the amino acid sequence of rat-derived urocortin(Ucn).

SEQ ID NO:9 is the nucleic acid sequence from which SEQ ID NO:8 was deduced.

SEQ ID NO:10 is the amino acid sequence of the rat-derived CRF receptor referred to as "rCRF-R1".

SEQ ID NO:11 is the amino acid sequence of a mouse-derived CRF receptor referred to as "mCRF-R2β".

SEQ ID NO:12 is the amino acid sequence of a rat-derived CRF receptor referred to as "rCRF-R2α".

SEQ ID NO:13 is the amino acid sequence of a rat-derived CRF receptor referred to as "rCRF-R2β".

SEQ ID NO:14 is the amino acid sequence of a 40-residue peptide defining certain analogs of Ucn.

SEQ ID NO:15 is the amino acid sequence of the precursor plus the mature human Ucn peptide.

SEQ ID NO:16 is the nucleic acid sequence from which SEQ ID NO:15 was deduced.

SEQ ID NO:17 is the amino acid sequence SEQ ID NO:8 with Tyr added at the N-terminus.

SEQ ID NO:18 is an oligo of 27 bases.

SEQ ID NO:19 is an oligo of 28 bases.

What is claimed is:

1. An isolated urocortin (Ucn) peptide which is characterized by
binding to corticotropin releasing factor (CRF) receptor 2 (CRF-R2) with a binding affinity ($K_D$) of 10 nanomolar or less,
increasing production of adrenocorticotropic hormone (ACTH), and
exhibiting higher affinity for the long form of CRF-R2 than does rat/human CRF (r/hCRF),
said peptide having the amino acid sequence of residues 83–122 of SEQ ID NO:15 or a sequence which differs by no more than 3 residues or a biologically functional fragment of either which increases production of ACTH.

2. A peptide according to claim 1 which is an N-terminally shortened functional fragment of the amino acid sequence of SEQ ID NO: 15 which increases production of ACTH wherein the C-terminus of said fragment is amidated.

3. A peptide according to claim 2 wherein the N-terminus is acylated.

4. A peptide according to claim 1 differing from residues 83–122 of SEQ ID NO:15 by substitution of 1, 2 or 3 residues wherein all said substitutions for residues in SEQ ID NO:15 are conservative substitutions.

5. A method of detecting a defect in ACTH secretion comprising
administering an effective dose of a peptide according to claim 1 to a human subject and monitoring the bloodstream of said subject for an increase in ACTH level, the failure to detect such an increase being indicative of a defect in ACTH secretion.

6. A pharmaceutical composition which comprises an effective amount of a peptide according to claim 1 in combination with a pharmaceutically acceptable carrier, which amount is effective to modulate the transactivation of CRF receptors or to increase intestinal transit rate.

7. A peptide which increases the production of ACTH having the following amino acid sequence (SEQ ID NO: 14):

Y-Xaa$_1$-Xaa$_2$-Pro-Xaa$_4$-Xaa$_5$-Ser-Xaa$_7$-Asp-Leu-Xaa$_{10}$-Xaa$_{11}$-Xaa$_{12}$-Xaa$_{13}$-Leu-Arg-Xaa$_{16}$-Xaa$_{17}$-Xaa$_{18}$-Xaa$_{19}$-Xaa$_{20}$-Xaa$_{21}$-Xaa$_{22}$-Xaa$_{23}$-Xaa$_{31}$-Xaa$_{32}$-Asn-Arg-Xaa$_{35}$-Xaa$_{36}$-Xaa$_{37}$-Xaa$_{38}$-Xaa$_{39}$-Xaa$_{40}$-NH$_2$, wherein Y is an acyl group having 7 or less carbon atoms or hydrogen; Xaa$_1$ is Asp, Glu or Gln; Xaa$_2$ is Asn, Asp, Glu or Gly; Xaa$_4$ is Ser or Pro; Xaa$_5$ is Leu, Ile or Met; Xaa$_7$ is Ile or Leu; Xaa$_{10}$ is Thr or Ser; Xaa$_{11}$ is Phe or Leu; Xaa$_{12}$ is His or Glu; Xaa$_{13}$ is Leu or Met; Xaa$_{16}$ is Thr, Asn, Glu, or Lys; Xaa$_{17}$ is Leu, Met or Val; Xaa$_{18}$ is Leu or Ile; Xaa$_{19}$ is Glu or His; Xaa$_{20}$ is Leu, Met, Ile or Arg; Xaa$_{21}$ is Ala, Glu or Thr; Xaa$_{22}$ is Arg or Lys; Xaa$_{23}$ is any natural amino acid other than Cys; Xaa$_{24}$ is Gln, Glu or Asp; Xaa$_{25}$ is any natural amino acid other than Cys; Xaa$_{26}$ is Gln, Leu or Glu; Xaa$_{27}$ is Arg, Ala or Lys; Xaa$_{28}$ is Glu or Gln; Xaa29 is Arg or Gln; Xaa$_{31}$ is any natural amino acid other than Cys; Xaa$_{32}$ is any natural amino acid other than Cys; Xaa$_{35}$ is Ile, Lys, Leu or Asn; Xaa$_{36}$ is Ile, Tyr, Met or Leu; Xaa$_{37}$ is Phe, Leu or Met; Xaa$_{38}$ is Asp or Glu; Xaa$_{39}$ is Ser, Ile, Glu or Thr; and Xaa$_{40}$ is Val, Ile, Phe or Ala; provided that there are no more than 3 residues different from hUcn (residues 83–122 of SEQ ID NO: 15) and that the N-terminus can be shortened by 1 or 2 residues.

8. A peptide according to claim 7 comprising an amino acid sequence having having no more than 3 residues which are different from the following amino acid sequence:

Y-R$_1$-Pro-Ser-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ (residues 85–122 of SEQ ID NO:15), wherein Y is an acyl group having 7 or less carbon atoms or hydrogen; and R$_1$ is Asn or desR$_1$.

9. Isolated DNA which encodes a urocortin (Ucn) peptide which is characterized by binding to corticotropin releasing factor (CRF) receptor 2 (CRF-R2) with a binding affinity (K$_D$) of 10 nanomolar or less, increasing production of adrenocorticotropic hormone (ACTH), and exhibiting higher affinity for the long form of CRF-R2 than does rat/human CRF (r/hCRF), said encoded peptide having the amino acid sequence of residues 83–122 of SEQ ID NO: 15 or a sequence which differs by no more than 3 residues or a biologically functional fragment of either which increases production of ACTH, or a fragment thereof comprising at least 14 contiguous nucleotides selected from nucleotides 247 to 366 of SEQ ID NO: 16 which is useful as a probe.

10. Isolated DNA according to claim 9 comprising DNA which has the nucleotide sequence as shown in SEQ ID NO:16 encoding residues 83–122 or a nucleotide sequence that encodes a peptide which differs therefrom by not more than 3 residues.

11. Isolated DNA according to claim 9 comprising nucleotide sequence SEQ ID NO:16 encoding residues 83–122.

12. A DNA probe according to claim 9 comprising at least 14 contiguous nucleotides of said isolated DNA selected from nucleotides 247 to 366 of SEQ ID NO: 16 which would not hybridize under high stringency conditions to DNA encoding known native CRFs, known native urotensins or native sauvagine but will hybridize under high stringency conditions to DNA encoding a biologically active Ucn-like peptide.

13. Isolated DNA according to claim 9 which encodes a biologically active Ucn-like peptide that is capable of hybridizing under high stringency conditions (such as would identify only sequences having at least 80% homology) to SEQ ID NO:16 and which would not hybridize under high stringency conditions to DNA encoding known CRFs, known urotensins or sauvagine, such high stringency conditions being minimally equivalent to hybridization in 50% formamide, 5×Denhart's solution, 5×SSPE, 0.2% SDS at 42° C., followed by washing in 0.2×SSPE, 0.2% SDS at 65° C.

14. Isolated DNA according to claim 9 which encodes a peptide comprising the amino acid sequence of residues 83–122 of SEQ ID NO: 15 or a sequence which differs by no more than 3 residues or a biologically functional fragment of either which increases production of ACTH.

15. A peptide which increases the production of ACTH having one of the following formulae:

H-Asp-Asn-Pro-Ser-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ (amino acids 83–122 of SEQ ID NO:15);

H-Asp-Asp-pro-pro-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ (SEQ ID NO:8);

H-Tyr-Asp-Asp-Pro-Pro-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ (SEQ ID NO:17);

H-D-Tyr-Asp-Asn-Pro-Ser-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$;

Ac-Pro-Ser-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ (amino acids 85–122 of SEQ ID NO:15);

H-Asn-Pro-Ser-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ (amino acids 84–122 of SEQ ID NO:15); or H-Asp-Asn-Pro-Ser-Leu-Ser-Ile-Asp-Leu-Thr-D-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$.

16. A peptide according to claim 15 having the formula: H-Asp-Asn-Pro-Ser-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ (amino acids 83–122 of SEQ ID NO:15).

17. A peptide according to claim 15 having the formula: H-Asp-Asp-Pro-Pro-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ (SEQ ID NO:8).

18. A peptide according to claim 15 having the formula: H-Asn-Pro-Ser-Leu-Ser-Ile-Asp-Leu-Thr-Phe-His-Leu-Leu-Arg-Thr-Leu-Leu-Glu-Leu-Ala-Arg-Thr-Gln-Ser-Gln-Arg-Glu-Arg-Ala-Glu-Gln-Asn-Arg-Ile-Ile-Phe-Asp-Ser-Val-NH$_2$ (amino acids 84–122 of SEQ ID NO:15); or H-Asp-Asn-Pro-Ser-Leu-Ser-Ile-Asp-Leu-Thr-D-Phe-His-Leu-Leu-Arg-Thr-Leu-Leu-Glu-Leu-Ala-Arg-Thr-Gln- Ser-Gln-Arg-Glu-Arg-Ala-Glu-Gln-Asn-Arg-Ile-Ile-Phe-Asp-Ser-Val-NH$_2$.

19. A peptide which increases the production of ACTH comprising the following amino acid sequence:

Y-Asp-R$_2$-Pro-R$_4$-Leu-Ser-Ile-Asp-Leu-Thr-D-Phe-His-Leu-Leu-Arg-Thr-Leu-Leu-R$_{19}$-Leu-Ala-Arg-Thr-Gln-Ser-Gln-Arg-Glu-R$_{29}$-Ala-Glu-R$_{32}$-Asn-Arg-Ile-R$_{36}$-Phe-R$_{38}$-Ser-Val-NH$_2$, wherein Y is an acyl group having 7 or less carbon atoms or hydrogen; R$_2$ is Asp or Asn; R$_4$ is Pro or Ser; R$_{19}$ is Glu or Ala; R$_{29}$ is Arg, Glu, Lys or Orn; R$_{32}$ is Gln, Lys, Orn or Glu; R$_{36}$ is Ile, C$^\alpha$MeIle or C$^\alpha$MeLeu; R$_{38}$ is Asp or Ala; provided that when R$_{29}$ is Glu, R$_{32}$ is either Lys or Orn and the side chains thereof are linked by an amide bond and that when R$_{32}$ is Glu, R$_{29}$ is either Lys or Orn and the side chains thereof are linked by an amide bond; and provided further that D-Phe$^{11}$ can be substituted by another D-isomer amino acid other than D-Cys; that Glu in the 31-position can be substituted by any D-isomer amino acid; and that the N-terminus can be shortened by 1 or 2 residues.

20. A peptide according to claim 19 which increases the production of ACTH comprising the following amino acid sequence:

Y-Asp-Asn-Pro-Ser-Leu-Ser-Ile-Asp-Leu-Thr-D-Phe-His-Leu-Leu-Arg-Thr-Leu-Leu-R$_{19}$-Leu-Ala-Arg-Thr-Gln-Ser-Gln-Arg-Glu-R$_{29}$-Ala-Glu-R$_{32}$-Asn-Arg-Ile-R$_{36}$-Phe-R$_{38}$-Ser-Val-NH$_2$, wherein Y is an acyl group having 7 or less carbon atoms or hydrogen; R$_{19}$ is Glu or Ala; R$_{29}$ is Arg, Glu, Lys or Orn; R$_{32}$ is Gln, Lys, Orn or Glu; R$_{36}$ is Ile, C$^\alpha$MeIle or C$^\alpha$MeLeu; R$_{38}$ is Asp or Ala; provided that when R$_{29}$ is Glu, R$_{32}$ is either Lys or Orn and the side chains thereof are linked by an amide bond and that when R$_{32}$ is Glu, R$_{29}$ is either Lys or Orn and the side chains thereof are linked by an amide bond; and provided further that D-Phe in the 11-position can be D-Leu or another D-amino acid; that Glu in the 31-position can be D-Glu or another D-amino acid; and that the N-terminus can be shortened by 1 or 2 residues.

21. A cyclic peptide according to claim 19 wherein R$_{29}$ is Glu and R$_{32}$ is Lys or Orn.

22. A cyclic peptide according to claim 19 having one of the following formulae:

(cyclo 29-32)
Ac-Pro-Ser-Leu-Ser-Ile-Asp-Leu-Thr-D-Phe-His-Leu-Leu-Arg-Thr-Leu-Leu-Glu-Leu-Ala-Arg-Thr-Gln-Ser-Gln-Arg- Glu-Glu-Ala-D-Glu-Lys-Asn-Arg-Ile-Ile-Phe-Asp-Ser-Val-NH$_2$;

(cyclo 29-32)
Ac-Pro-D-Pro-Leu-Ser-Ile-Asp-Leu-Thr-D-Phe-His-Leu-Leu-Arg-Thr-

Leu-Leu-Glu-Leu-Ala-Arg-Thr-Gln-Ser-Gln-Arg-Glu-Glu-Ala-Glu-Ly:
Asn-Arg-Ile-Ile-Phe-Asp-Ser-Val-NH$_2$; and (cyclo 29-32)
Ac-Pro-D-Ser-Leu-Ser-Ile-Asp-Leu-Thr-D-Phe-His-Leu-Leu-Arg-Thr- Leu-Leu-Glu-Leu-Ala-Arg-Thr-Gln-Ser-Gln-Arg-Glu-Glu-Ala-Glu-Ly:
Asn-Arg-Ile-Ile-Phe-Asp-Ser-Val-NH$_2$.

* * * * *

UNITED STATES PATENT AND TRADEMARK OFFICE
CERTIFICATE OF CORRECTION

PATENT NO. : 6,214,797 B1
DATED : April 10, 2001
INVENTOR(S) : Vale, Jr. et al.

Page 1 of 1

It is certified that error appears in the above-identified patent and that said Letters Patent is hereby corrected as shown below:

Column 59, claim 7
Line 6, should read "$Xaa_{20}$-$Xaa_{21}$-$Xaa_{22}$-$Xaa_{23}$-$Xaa_{24}$-$Xaa_{25}$-$Xaa_{26}$-$Xaa_{27}$-$Xaa_{28}$-$Xaa_{29}$-Ala-$Xaa_{31}$-$Xaa_{32}$-Asn-Arg-$Xaa_{35}$-".

Column 62, claim 22,
At the end of line 21, change "Ly" to -- Lys- --.
At the end of line 26, change "Ly" to -- Lys- --.

Signed and Sealed this

Twenty-fifth Day of December, 2001

Attest:

Attesting Officer

JAMES E. ROGAN
Director of the United States Patent and Trademark Office